US012672916B2

(12) United States Patent
Shelton, IV et al.

(10) Patent No.: US 12,672,916 B2
(45) Date of Patent: Jul. 7, 2026

(54) SURGICAL COMPUTING SYSTEM WITH INTERMEDIATE MODEL SUPPORT

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 480 days.

(21) Appl. No.: 18/092,026

(22) Filed: Dec. 30, 2022

(65) Prior Publication Data

US 2024/0216065 A1 Jul. 4, 2024

(51) Int. Cl.
*A61B 34/10* (2016.01)
*A61B 34/20* (2016.01)
*G06N 3/02* (2006.01)

(52) U.S. Cl.
CPC .............. *A61B 34/10* (2016.02); *A61B 34/20* (2016.02); *A61B 2034/105* (2016.02)

(58) Field of Classification Search
None
See application file for complete search history.

(56) References Cited

U.S. PATENT DOCUMENTS

| | | |
|---|---|---|
| 9,345,481 B2 | 5/2016 | Hall et al. |
| 9,687,230 B2 | 6/2017 | Leimbach et al. |
| 10,390,895 B2 | 8/2019 | Henderson et al. |

(Continued)

FOREIGN PATENT DOCUMENTS

| | | |
|---|---|---|
| CN | 108430339 A | 8/2018 |
| CN | 108511057 A | 9/2018 |
| WO | 2021113168 A1 | 6/2021 |

OTHER PUBLICATIONS

Alsallal, et al., "A Machine Learning Technique to Detect Counterfeit Medicine Based on X-Ray Fluorescence Analyser", International Conference On Computing, Electronics & Communications Engineering (ICCECE), IEEE, 2018, pp. 118-122.

(Continued)

*Primary Examiner* — Beniyam Menberu

(74) *Attorney, Agent, or Firm* — Condo Roccia Koptiw LLP

(57) ABSTRACT

A surgical computing device may include a processor configured to implement two neural networks, a primary neural network trained with a procedure focus and support neural network trained with a patient focus. Data indicative of a surgical patient, a target procedure, and a proposed procedure plan may be input to the support neural network. The support neural network may generate a patient specific mapping from this data. The patient specific mapping and the data indicative of a surgical patient, a target procedure, and a proposed procedure plan may be input to the primary neural network. The primary neural network may output a modified procedure plan that is different from the proposed procedure plan. In an example, the support neural network is trained to isolate anatomical elements. And the primary neural network is trained to identify procedure plans associated with improved patient outcomes. Such a two-network approach may facilitate the use of diverse training data sets to better refine procedure plans for a variety of uses.

20 Claims, 18 Drawing Sheets

(56) References Cited

U.S. PATENT DOCUMENTS

| 10,695,081 | B2 | 6/2020 | Shelton, IV et al. | |
| 10,842,523 | B2 | 11/2020 | Shelton, IV et al. | |
| 10,881,399 | B2 | 1/2021 | Shelton, IV et al. | |
| 10,932,808 | B2 | 3/2021 | Shelton, IV et al. | |
| 11,158,415 | B2 * | 10/2021 | Daley | A61B 5/0082 |
| 11,410,259 | B2 | 8/2022 | Harris et al. | |
| 11,423,007 | B2 | 8/2022 | Shelton, IV et al. | |
| 11,464,590 | B1 | 10/2022 | Roh et al. | |
| 2007/0027459 | A1 | 2/2007 | Horvath et al. | |
| 2008/0285626 | A1 | 11/2008 | Ma et al. | |
| 2010/0228222 | A1 | 9/2010 | Williams et al. | |
| 2011/0112384 | A1 | 5/2011 | Eisenhardt et al. | |
| 2013/0211792 | A1 * | 8/2013 | Kang | A61B 34/30 |
| | | | | 703/1 |
| 2013/0218163 | A1 * | 8/2013 | Frey | A61B 17/1671 |
| | | | | 606/86 R |
| 2014/0005743 | A1 | 1/2014 | Giuffrida et al. | |
| 2014/0263552 | A1 | 9/2014 | Hall et al. | |
| 2014/0270423 | A1 * | 9/2014 | Zellner | G16H 20/40 |
| | | | | 382/128 |
| 2017/0202605 | A1 | 7/2017 | Shelton, IV et al. | |
| 2017/0296213 | A1 | 10/2017 | Swensgard et al. | |
| 2017/0360512 | A1 | 12/2017 | Couture et al. | |
| 2018/0049822 | A1 | 2/2018 | Henderson et al. | |
| 2018/0221093 | A1 * | 8/2018 | Hladio | A61B 90/39 |
| 2018/0360452 | A1 | 12/2018 | Shelton, IV et al. | |
| 2019/0006047 | A1 | 1/2019 | Gorek et al. | |
| 2019/0059929 | A1 | 2/2019 | Shelton, IV et al. | |
| 2019/0073632 | A1 | 3/2019 | Laster et al. | |
| 2019/0104919 | A1 | 4/2019 | Shelton, IV et al. | |
| 2019/0125455 | A1 | 5/2019 | Shelton, IV et al. | |
| 2019/0200844 | A1 | 7/2019 | Shelton, IV et al. | |
| 2019/0200981 | A1 | 7/2019 | Harris et al. | |
| 2019/0200997 | A1 | 7/2019 | Shelton, IV et al. | |
| 2019/0201047 | A1 | 7/2019 | Yates et al. | |
| 2019/0201119 | A1 | 7/2019 | Harris et al. | |
| 2019/0201123 | A1 | 7/2019 | Shelton, IV et al. | |
| 2019/0201136 | A1 | 7/2019 | Shelton, IV et al. | |
| 2019/0201137 | A1 | 7/2019 | Shelton, IV et al. | |
| 2019/0201144 | A1 | 7/2019 | Shelton, IV et al. | |
| 2019/0205567 | A1 | 7/2019 | Shelton, IV et al. | |
| 2019/0206555 | A1 | 7/2019 | Morgan et al. | |
| 2019/0206562 | A1 | 7/2019 | Shelton, IV et al. | |
| 2019/0206564 | A1 | 7/2019 | Shelton, IV et al. | |
| 2019/0206569 | A1 | 7/2019 | Shelton, IV et al. | |
| 2019/0207857 | A1 | 7/2019 | Shelton, IV et al. | |
| 2019/0272917 | A1 * | 9/2019 | Couture | G06N 20/00 |
| 2020/0015901 | A1 | 1/2020 | Scheib et al. | |
| 2020/0237452 | A1 | 7/2020 | Wolf et al. | |
| 2020/0345431 | A1 * | 11/2020 | Patton | A61B 34/25 |
| 2020/0405296 | A1 | 12/2020 | Shelton, IV et al. | |
| 2021/0082579 | A1 * | 3/2021 | Grady | G16H 50/50 |
| 2021/0196384 | A1 | 7/2021 | Shelton, IV et al. | |
| 2021/0210189 | A1 | 7/2021 | Casey et al. | |
| 2021/0244487 | A1 | 8/2021 | Beck | |
| 2021/0307765 | A1 * | 10/2021 | Dumpe | A61B 34/20 |
| 2021/0315579 | A1 | 10/2021 | Shelton, IV et al. | |
| 2021/0322014 | A1 | 10/2021 | Shelton, IV et al. | |
| 2021/0343017 | A1 | 11/2021 | Jordan | |
| 2021/0344880 | A1 | 11/2021 | Katra et al. | |
| 2021/0370790 | A1 | 12/2021 | Feldman | |
| 2022/0096163 | A1 | 3/2022 | Payyavula et al. | |
| 2022/0104822 | A1 | 4/2022 | Shelton, IV et al. | |
| 2022/0160443 | A1 * | 5/2022 | Spykerman | G16H 30/40 |
| 2022/0233119 | A1 | 7/2022 | Shelton, IV et al. | |
| 2022/0233191 | A1 * | 7/2022 | Shelton, IV | G16H 40/63 |
| 2022/0238216 | A1 | 7/2022 | Shelton, IV et al. | |
| 2022/0286687 | A1 | 9/2022 | Bishop et al. | |
| 2022/0313362 | A1 * | 10/2022 | Casey | A61F 2/4455 |
| 2022/0331047 | A1 | 10/2022 | Shelton, IV et al. | |
| 2022/0367040 | A1 | 11/2022 | Sutherland et al. | |
| 2022/0370138 | A1 | 11/2022 | Shelton, IV et al. | |
| 2022/0392621 | A1 | 12/2022 | George et al. | |
| 2022/0409140 | A1 * | 12/2022 | Cordonnier | G16H 30/20 |
| 2023/0028948 | A1 * | 1/2023 | Rolls | G16H 50/70 |
| 2023/0095002 | A1 | 3/2023 | Shelton, IV et al. | |
| 2023/0097906 | A1 | 3/2023 | Shelton, IV et al. | |
| 2023/0098538 | A1 | 3/2023 | Shelton, IV et al. | |
| 2023/0326193 | A1 | 10/2023 | Zia et al. | |
| 2023/0352133 | A1 | 11/2023 | Chen et al. | |
| 2023/0377709 | A1 | 11/2023 | Shelton, IV et al. | |
| 2024/0024027 | A1 | 1/2024 | Shelton et al. | |
| 2024/0029858 | A1 * | 1/2024 | Upadrasta | G16H 20/40 |
| 2024/0049944 | A1 * | 2/2024 | Kobayashi | A61B 5/489 |
| 2024/0065550 | A1 | 2/2024 | Connor | |
| 2024/0112768 | A1 | 4/2024 | Shelton, IV et al. | |
| 2024/0138919 | A1 * | 5/2024 | Casey | G16H 20/40 |
| 2024/0197173 | A1 * | 6/2024 | Kok | A61B 34/25 |
| 2024/0216065 | A1 | 7/2024 | Shelton, IV et al. | |
| 2024/0216081 | A1 | 7/2024 | Shelton, IV et al. | |
| 2024/0220763 | A1 | 7/2024 | Shelton, IV et al. | |
| 2024/0221878 | A1 | 7/2024 | Shelton, IV et al. | |
| 2024/0221892 | A1 | 7/2024 | Shelton, IV et al. | |
| 2024/0221893 | A1 | 7/2024 | Shelton, IV et al. | |
| 2024/0221894 | A1 | 7/2024 | Shelton, IV et al. | |
| 2024/0221895 | A1 | 7/2024 | Shelton, IV et al. | |
| 2024/0221896 | A1 | 7/2024 | Shelton, IV et al. | |
| 2024/0221897 | A1 | 7/2024 | Shelton, IV et al. | |
| 2024/0221923 | A1 | 7/2024 | Shelton, IV et al. | |
| 2024/0221924 | A1 | 7/2024 | Shelton, IV et al. | |
| 2024/0221931 | A1 | 7/2024 | Shelton, IV et al. | |
| 2024/0221937 | A1 | 7/2024 | Shelton, IV et al. | |
| 2024/0221960 | A1 | 7/2024 | Shelton, IV et al. | |

OTHER PUBLICATIONS

Anonymous, "Cloud computing", Wikipedia, the free encyclopedia, Dec. 22, 2022, pp. 1-24.

Asadizanjani, et al., "Counterfeit Electronics Detection Using Image Processing and Machine Learning", Journal of Physics Conference Series, vol. 787, 2017, pp. 1-6.

Domingues, "Using Deep Learning Techniques in Medical Imaging: A Systematic Review of Applications on CT and PET", Artificial Intelligence Review, Nov. 21, 2019, pp. 4093-4160.

Qayyum, "Secure and Robust Machine Learning for Healthcare: A Survey", IEEE, Reviews In Biomedical Engineering, vol. 14, 2021, 156-180.

Unberath, "The Impact of Machine Learning on 2D/3D Registration for Image-Guided Interventions: A Systemic Review and Perspective", Frontiers in Robotics and AI, vol. 8, No. 716007, Aug. 30, 2021, pp. 1-24.

Qayyum, et al., "Secure and Robust Machine Learning for Healthcare: A Survey", IEEE Reviews In Biomedical Engineering, vol. 14, 2021, 25 pages.

Domingues, et al., "Using deep learning techniques in medical imaging: a systematic review of applications on CT and PET", Artificial Intelligence Review, Springer Nature B.V., published Nov. 21, 2019.

Unberath, et al. "The Impact of Machine Learning on 2D/3D Registration for Image-Guided Interventions: A Systemic Review and Perspective", Frontiers in Robotics and AI, Systematic Review, Published Aug. 30, 2021, 24 pages.

Brownlee, Jason , "Dynamic Ensemble Selection (DES) for Classification in Python—MachineLearningMastery.com", Retrieved from the Internet: URL: https://web.archive.org/web/20221206025245/https://machinelearningmastery.com/dynamic-ensemble-selection-in-python/XP093167838, Dec. 6, 2022, pp. 1-3.

ISO 26262-1, "Road Vehicle—Functional Safety—Part 1: Vocabulary", International Organization for Standardization, Edition 2, Dec. 2018, 13 pages.

Bell, "Introduction & revision of IEC 61508", Measurement + Control vol. 42/6, Ron Bell Consulting Lt., UK, Jul. 2009, 6 pages.

* cited by examiner

_750_

51000

SURGICAL COMPUTING SYSTEM WITH INTERMEDIATE MODEL SUPPORT

CROSS-REFERENCE TO RELATED APPLICATIONS

This application is related to the concurrently filed U.S. Patent Applications, the content, in its entirety, of each is hereby incorporated by reference herein:

U.S. patent application Ser. No. 18/092,025, concurrently filed and entitled, "A Method for Advanced Algorithm Support"

BACKGROUND

Patient care is generally improved when tailored to the individual. Every person has different needs, so surgical and interventional solutions that center on the unique journey of every patient may represent efficient, groundbreaking pathways to healing. At the same time, the high stakes of patient care, in particular surgical processes, often drive a focus on conservative, repeatable activities.

Innovative medical technology, such as advanced surgical support computing systems and intelligent surgical instruments for example, may improve approaches to patient care and address the particular needs of health care providers.

The ever-increasing availability data and computing resources have made non-traditional algorithms, such as machine learning algorithms, a specific technical opportunity in health care systems. But incorporating such non-traditional algorithms into any medical technology presents many challenges.

Surgical data may be prepared and processed in order to determine surgical procedures, or plans, for example to inform one or more steps of future surgical procedures to improve surgical outcomes. However, surgical data encompasses a wide range of data types from a myriad of data sources, including data related to the context and scope of the surgery itself, data related to the configuration and/or control of the devices to be used in surgery and/or data generated during surgery. The amount and variation of surgical data can make such data difficult to process for the purposes of enhancing surgical plans and procedures or making surgical recommendations. Historic surgical data may be used for these purposes. For example, historical surgical data may be used to make surgical plans or recommendations, including for one or more steps of future surgical procedures, based on how the one or more steps were previously performed. Yet, using traditional analysis of surgical data, it can often be difficult to identify trends, particularly complex trends, in the data. For this reason traditional techniques for analysing surgical data may lack accuracy.

SUMMARY

A surgical computing device may include a processor. The processor may be configured to implement two neural networks, a primary neural network trained with a procedure focus and support neural network trained with a patient focus. Data indicative of a surgical patient, a target procedure, and a proposed procedure plan may be input to the support neural network. The support neural network may generate a patient specific mapping from this data. The patient specific mapping and the data indicative of a surgical patient, a target procedure, and a proposed procedure plan may be input to the primary neural network. The primary neural network may output a modified procedure plan that is different from the proposed procedure plan.

In an example, the support neural network is trained to isolate anatomical elements. And the primary neural network is trained to identify procedure plans associated with improved patient outcomes. The support neural network and the primary neural network may be independently trained.

Such a two-network approach may facilitate the use of diverse training data sets to better refine procedure plans for a variety of uses. For example, the modified procedure plan may identify a port location different than that identified in by the proposed procedure plan. For example, the modified procedure plan may identify a surgical instrument different than that identified by the proposed procedure plan. For example, the modified procedure plan may identify a tumor margin different than that identified by the proposed procedure plan. For example, the modified procedure plan may identify a mobilization approach different than that identified by the proposed procedure plan.

DETAILED DESCRIPTION

Figure 1:
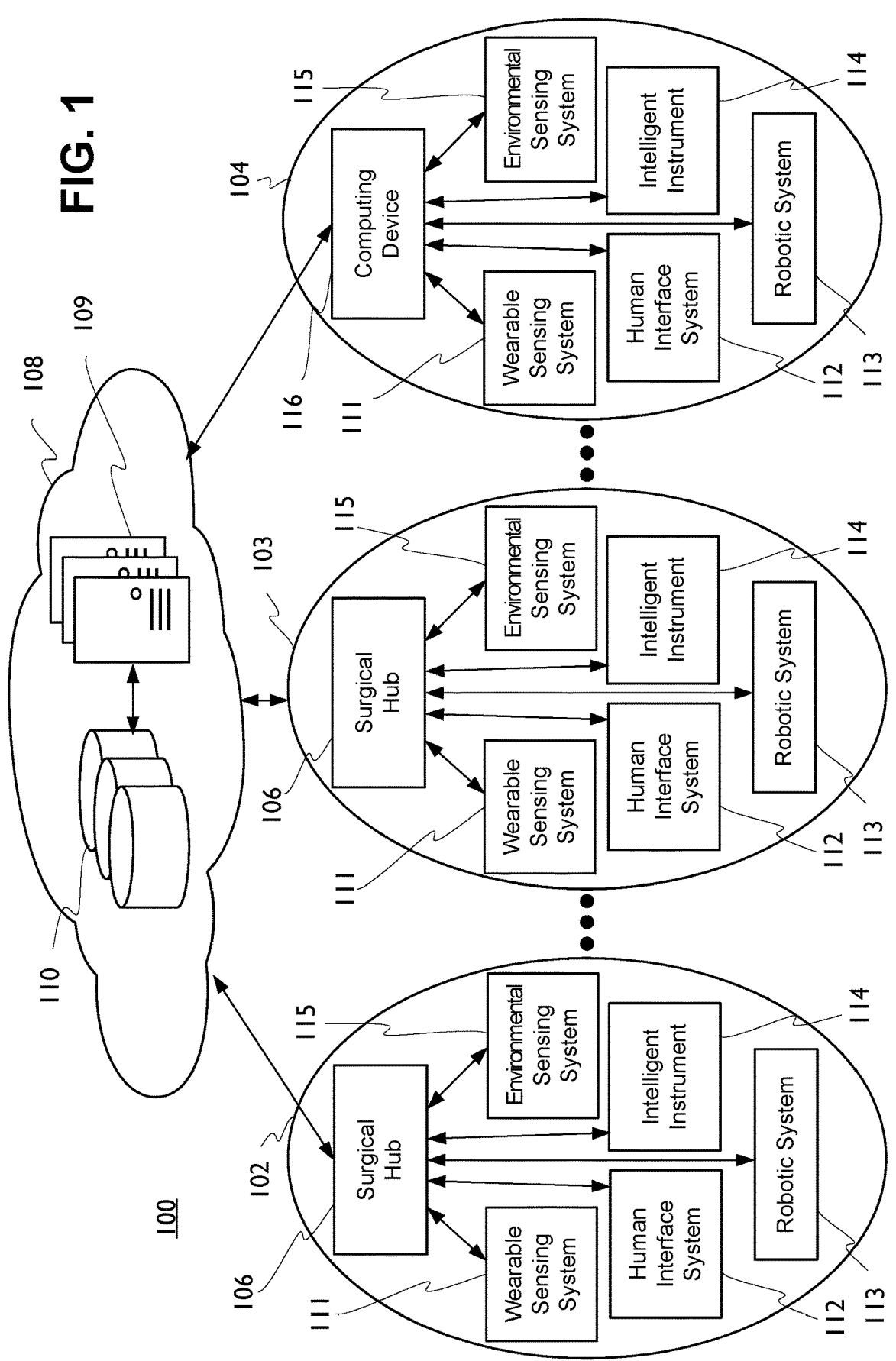
FIG. 1 is a block diagram of a computer-implemented surgical system.

FIG. 1 is a block diagram of a computer-implemented surgical system 100. An example surgical system, such as the surgical system 100, may include one or more surgical systems (e.g., surgical sub-systems) 102, 103, 104. For example, surgical system 102 may include a computer-implemented interactive surgical system. For example, surgical system 102, 103, 104 may include a surgical computing system, such as surgical hub 106 and/or computing device 116, in communication with a cloud computing system 108. The cloud computing system 108 may include a cloud server 109 and a cloud storage unit 110.

Surgical systems 102, 103, 104 may each computer-enabled surgical equipment and devices. For example, surgical systems 102, 103, 104 may include a wearable sensing system 111, a human interface system 112, a robotic system 113, one or more intelligent instruments 114, environmental sensing system 115, and/or the like. The wearable sensing system 111 may include one or more devices used to sense aspects of individuals status and activity within a surgical environment. For example, the wearable sensing system 111 may include health care provider sensing systems and/or patient sensing systems.

The human interface system 112 may include devices that enable an individual to interact with the surgical system 102, 103, 104 and/or the cloud computing system 108. The human interface system 112 may include a human interface device.

The robotic system 113 may include surgical robotic devices, such a surgical robot. The robotic system 113 may enable robotic surgical procedures. The robotic system 113 may receive information, settings, programming, controls and the like from the surgical hub 106 for example, the robotic system 113 may send data, such as sensor data, feedback information, video information, operational logs, and the like to the surgical hub 106.

Figure 2:
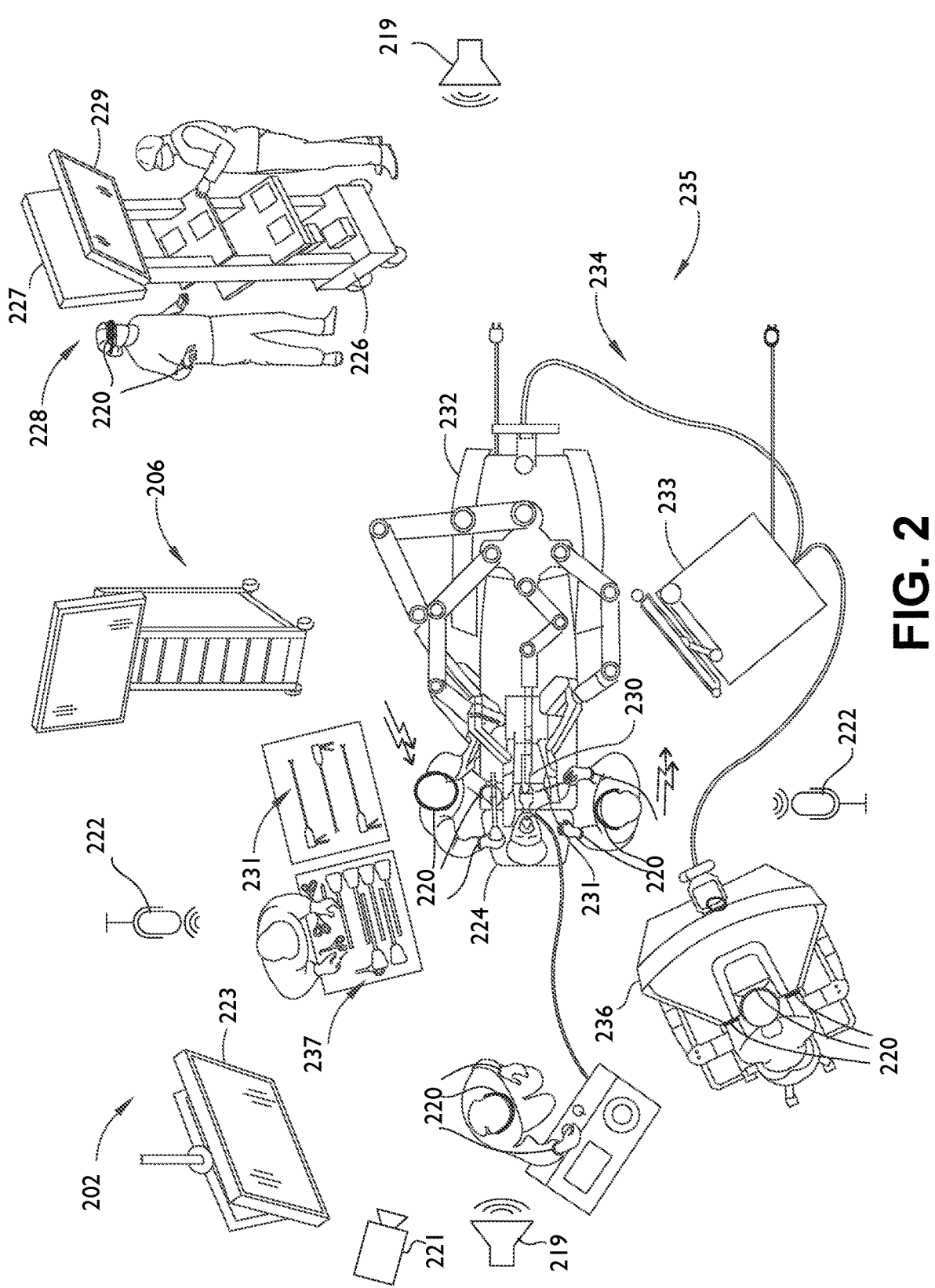
FIG. 2 shows an example surgical system in a surgical operating room.

The environmental sensing system 115 may include one or more devices, for example, used for measuring one or more environmental attributes, for example, as further described in FIG. 2. The robotic system 113 may include a plurality of devices used for performing a surgical procedure, for example, as further described in FIG. 2.

The surgical system 102 may be in communication with a remote server 109 that may be part of a cloud computing system 108. In an example, the surgical system 102 may be in communication with a remote server 109 via networked connection, such an internet connection (e.g., business internet service, T3, cable/FIOS networking node, and the like). The surgical system 102 and/or a component therein may communicate with the remote servers 109 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, the surgical hub 106 may facilitate displaying the image from an surgical imaging device, like a laparoscopic scope for example. The surgical hub 106 have cooperative interactions with the other local systems to facilitate displaying information relevant to those local systems. The surgical hub 106 may interact with one or more sensing systems 111, 115, one or more intelligent instruments 114, and/or multiple displays. For example, the surgical hub 106 may be configured to gather measurement data from the one or more sensing systems 111, 115 and send notifications or control messages to the one or more sensing systems 111, 115. The surgical hub 106 may send and/or receive information including notification information to and/or from the human interface system 112. The human interface system 112 may include one or more human interface devices (HIDs). The surgical hub 106 may send and/or receive notification information or control information to audio, display and/or control information to various devices that are in communication with the surgical hub.

For example, the sensing systems 111, 115 may include the wearable sensing system 111 (which may include one or more HCP sensing systems and one or more patient sensing systems) and the environmental sensing system 115. The one or more sensing systems 111, 115 may measure data relating to various biomarkers. The one or more sensing systems 111, 115 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiogramactroencephalography, colorimetry, impedimentary, potentiometry, amperometry, etc.

The biomarkers measured by the one or more sensing systems 111, 115 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 100, for example. The information from the biomarkers may be determined and/or used by the computer-implemented patient and the surgical system 100 to improve said systems and/or to improve patient outcomes, for example. The one or more sensing systems 111, 115, biomarkers, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

FIG. 2 shows an example of a surgical system 202 in a surgical operating room. As illustrated in FIG. 2, a patient is being operated on by one or more health care professionals (HCPs). The HCPs are being monitored by one or more HCP sensing systems 220 worn by the HCPs. The HCPs and the environment surrounding the HCPs may also be monitored by one or more environmental sensing systems including, for example, a set of cameras 221, a set of microphones 222, and other sensors that may be deployed in the operating room. The HCP sensing systems 220 and the environmental sensing systems may be in communication with a surgical hub 206, which in turn may be in communication with one or more cloud servers 209 of the cloud computing system 208, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 223 and one or more audio output devices (e.g., speakers 219) are positioned in the sterile field to be visible to an operator at the operating table 224. In addition, a visualization/notification tower 226 is positioned outside the sterile field. The visualization/notification tower 226 may include a first non-sterile human interactive device (HID) 227 and a second non-sterile HID 229, which may face away from each other. The HID may be a display or a display with a touchscreen allowing a human to interface directly with the HID. A human interface system, guided by the surgical hub 206, may be configured to utilize the HIDs 227, 229, and 223 to coordinate information flow to operators inside and outside the sterile field. In an example, the surgical hub 206 may cause an HID (e.g., the primary HID 223) to display a notification and/or information about the patient and/or a surgical procedure step. In an example, the surgical hub 206 may prompt for and/or receive input from personnel in the sterile field or in the non-sterile area. In an example, the surgical hub 206 may cause an HID to display a snapshot of a surgical site, as recorded by an imaging device 230, on a non-sterile HID 227 or 229, while maintaining a live feed of the surgical site on the primary HID 223. The snapshot on the non-sterile display 227 or 229 can permit a non-sterile operator to perform a diagnostic step relevant to the surgical procedure, for example.

In one aspect, the surgical hub 206 may be configured to route a diagnostic input or feedback entered by a non-sterile operator at the visualization tower 226 to the primary display 223 within the sterile field, where it can be viewed by a sterile operator at the operating table. In one example, the input can be in the form of a modification to the snapshot displayed on the non-sterile display 227 or 229, which can be routed to the primary display 223 by the surgical hub 206.

Referring to FIG. 2, a surgical instrument 231 is being used in the surgical procedure as part of the surgical system 202. The hub 206 may be configured to coordinate information flow to a display of the surgical instrument 231. For example, in U.S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 226 can be routed by the hub 206 to the surgical instrument display within the sterile field, where it can be viewed by the operator of the surgical instrument 231. Example surgical instruments that are suitable for use with the surgical system 202 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 202 being used to perform a surgical procedure on a patient who is lying down on an operating table 224 in a surgical operating room 235. A robotic system 234 may be used in the surgical procedure as a part of the surgical system 202. The robotic system 234 may include a surgeon's console 236, a patient side cart 232 (surgical robot), and a surgical robotic hub 233. The patient side cart 232 can manipulate at least one removably coupled surgical tool 237 through a minimally invasive incision in the body of the patient while the surgeon views the surgical site through the surgeon's console 236. An image of the surgical site can be obtained by a medical imaging device 230, which can be manipulated by the patient side cart 232 to orient the imaging device 230. The robotic hub 233 can be used to process the images of the surgical site for subsequent display to the surgeon through the surgeon's console 236.

Other types of robotic systems can be readily adapted for use with the surgical system 202. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 208, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 230 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 230 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 230 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 230 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 211 illustrated in FIG. 1 may include one or more sensing systems, for example, HCP sensing systems 220 as shown in FIG. 2. The HCP sensing systems 220 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 220 may measure a set of biomarkers to monitor the heart rate of an HCP. In an example, a sensing system 220 worn on a surgeon's wrist (e.g., a watch or a wristband) may use an accelerometer to detect hand motion and/or shakes and determine the magnitude and frequency of tremors. The sensing system 220) may send the measurement data associated with the set of biomarkers and the data associated with a physical state of the surgeon to the surgical hub 206 for further processing. One or more environmental sensing devices may send environmental information to the surgical hub 206. For example, the environmental sensing devices may include a camera 221 for detecting hand/body position of an HCP. The environmental sensing devices may include microphones 222 for measuring the ambient noise in the surgical theater. Other environmental sensing devices may include devices, for example, a thermometer to measure temperature and a hygrometer to measure humidity of the surroundings in the surgical theater, etc. The surgical hub 206, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 220 may measure one or more surgeon biomarkers associated with an HCP and send the measurement data associated with the surgeon biomarkers to the surgical hub 206. The HCP sensing systems 220 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 206 may use the surgeon biomarker measurement data associated with an HCP to adaptively control one or more surgical instruments 231. For example, the surgical hub 206 may send a control program to a surgical instrument 231 to control its actuators to limit or compensate for fatigue and use of fine motor skills. The surgical hub 206 may send the control program based on situational awareness and/or the context on importance or criticality of a task. The control program may instruct the instrument to alter operation to provide more control when control is needed.

Figure 3:
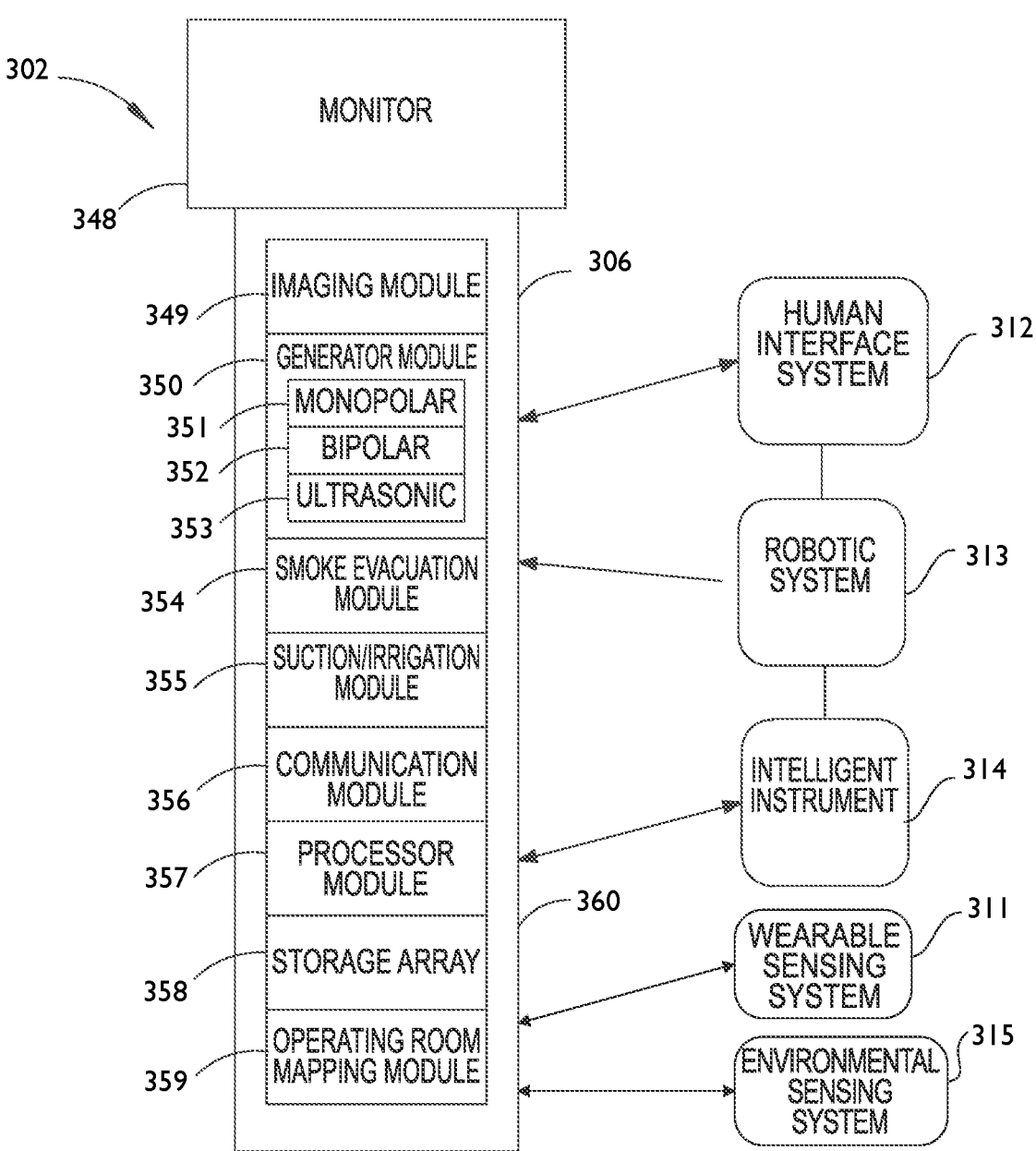
FIG. 3 illustrates an example surgical hub paired with various systems.

FIG. 3 shows an example surgical system 302 with a surgical hub 306. The surgical hub 306 may be paired with, via a modular control, a wearable sensing system 311, an environmental sensing system 315, a human interface system 312, a robotic system 313, and an intelligent instrument 314. The hub 306 includes a display 348, an imaging module 349, a generator module 350, a communication module 356, a processor module 357, a storage array 358, and an operating-room mapping module 359. In certain aspects, as illustrated in FIG. 3, the hub 306 further includes a smoke evacuation module 354 and/or a suction/irrigation module 355. The various modules and systems may be connected to the modular control either directly via a router or via the communication module 356. The operating theater devices may be coupled to cloud computing resources and data storage via the modular control. The human interface system 312 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 360 offers a unified environment for managing the power, data, and fluid lines, which reduces the frequency of entanglement between such lines. Aspects of the present disclosure present a surgical hub 306 for use in a surgical procedure that involves energy application to tissue at a surgical site.

The surgical hub 306 includes a hub enclosure 360 and a combo generator module slidably receivable in a docking station of the hub enclosure 360. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 355 slidably received in the hub enclosure 360. In one aspect, the hub enclosure 360 may include a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 360 is configured to accommodate different generators and facilitate an interactive communication therebetween. The hub modular enclosure 360 may enable the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 360 that allows the modular integration of a generator module 350, a smoke evacuation module 354, and a suction/irrigation module 355. The hub modular enclosure 360 further facilitates interactive communication between the modules 359, 354, and 355. The generator module 350 can be with integrated monopolar, bipolar, and ultrasonic components supported in a single housing unit slidably insertable into the hub modular enclosure 360. The generator module 350 can be configured to connect to a monopolar device 351, a bipolar device 352, and an ultrasonic device 353. Alternatively, the generator module 350 may comprise a series of monopolar, bipolar, and/or ultrasonic generator modules that interact through the hub modular enclosure 360. The hub modular enclosure 360 can be configured to facilitate the insertion of multiple generators and interactive communication between the generators docked into the hub modular enclosure 360 so that the generators would act as a single generator.

Figure 4:
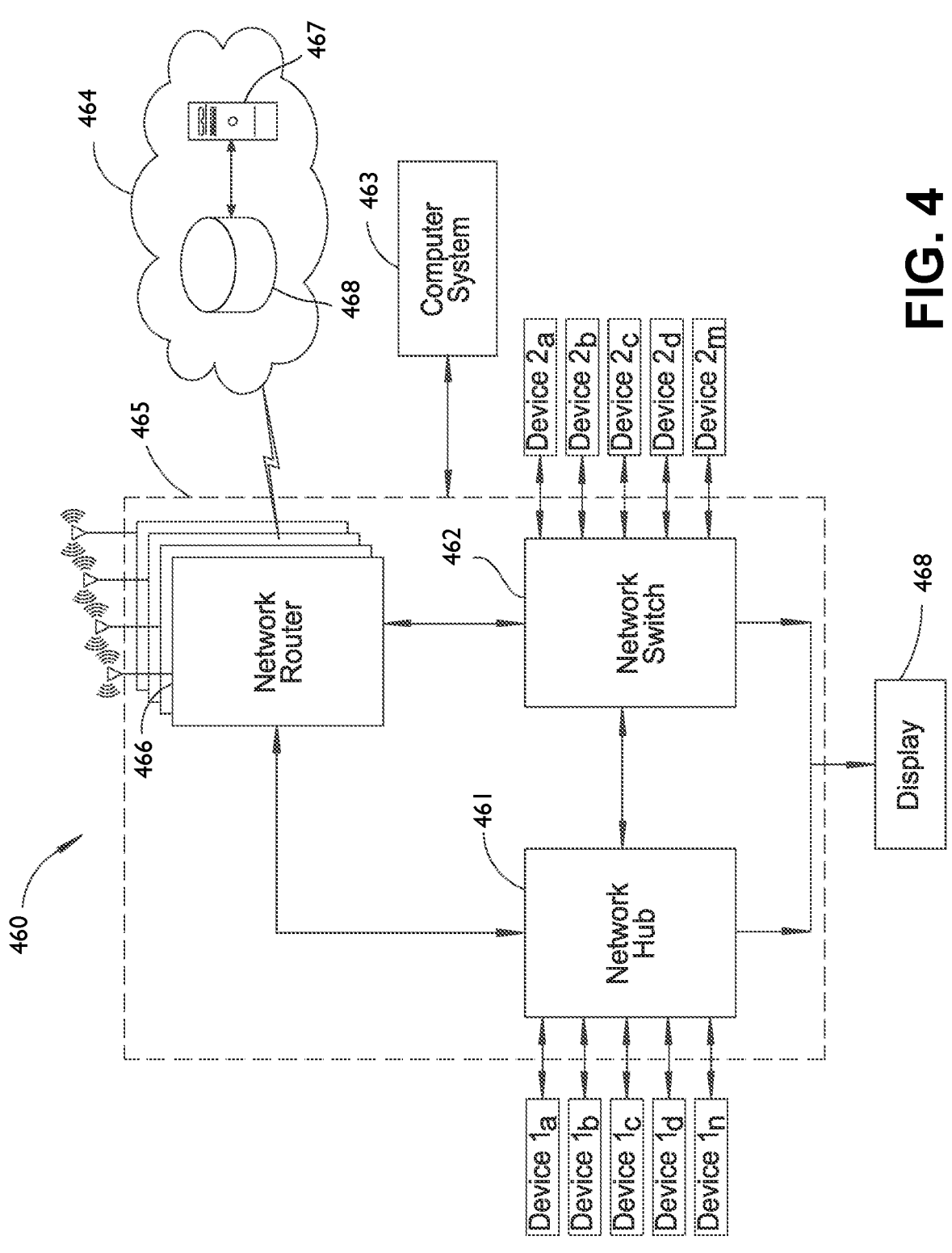
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 460 may include a modular communication hub 465 that is configured to connect modular devices located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system 463 to provide local computer processing and data manipulation.

The computer system 463 may comprise a processor and a network interface. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellaris WareR software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 463 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 463 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system 463 and to output information from the computer system 463 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 463 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 463 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 463, it can also be external to the computer system 463. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 460 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 461 or network switch 462. An intelligent surgical data network may be referred to as a manageable hub or switch. A switching hub reads the destination address of each packet and then forwards the packet to the correct port.

Modular devices 1a-1n located in the operating theater may be coupled to the modular communication hub 465. The network hub 461 and/or the network switch 462 may be coupled to a network router 466 to connect the devices 1a-In to the cloud computing system 464 or the local computer system 463. Data associated with the devices 1a-1n may be transferred to cloud-based computers via the router for remote data processing and manipulation. Data associated with the devices 1a-1n may also be transferred to the local computer system 463 for local data processing and manipulation. Modular devices 2a-2m located in the same operating theater also may be coupled to a network switch 462. The network switch 462 may be coupled to the network hub 461 and/or the network router 466 to connect the devices 2a-2m to the cloud 464. Data associated with the devices 2a-2m may be transferred to the cloud computing system 464 via the network router 466 for data processing and manipulation. Data associated with the devices 2a-2m may also be transferred to the local computer system 463 for local data processing and manipulation.

As illustrated in FIG. 4 a computing system, such as a surgical hub system 460, may include a modular communication hub 465 that is configured to connect modular devices (e.g., surgical devices) located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system (e.g., a computing device) to provide local computer processing and data manipulation.

Figure 5:
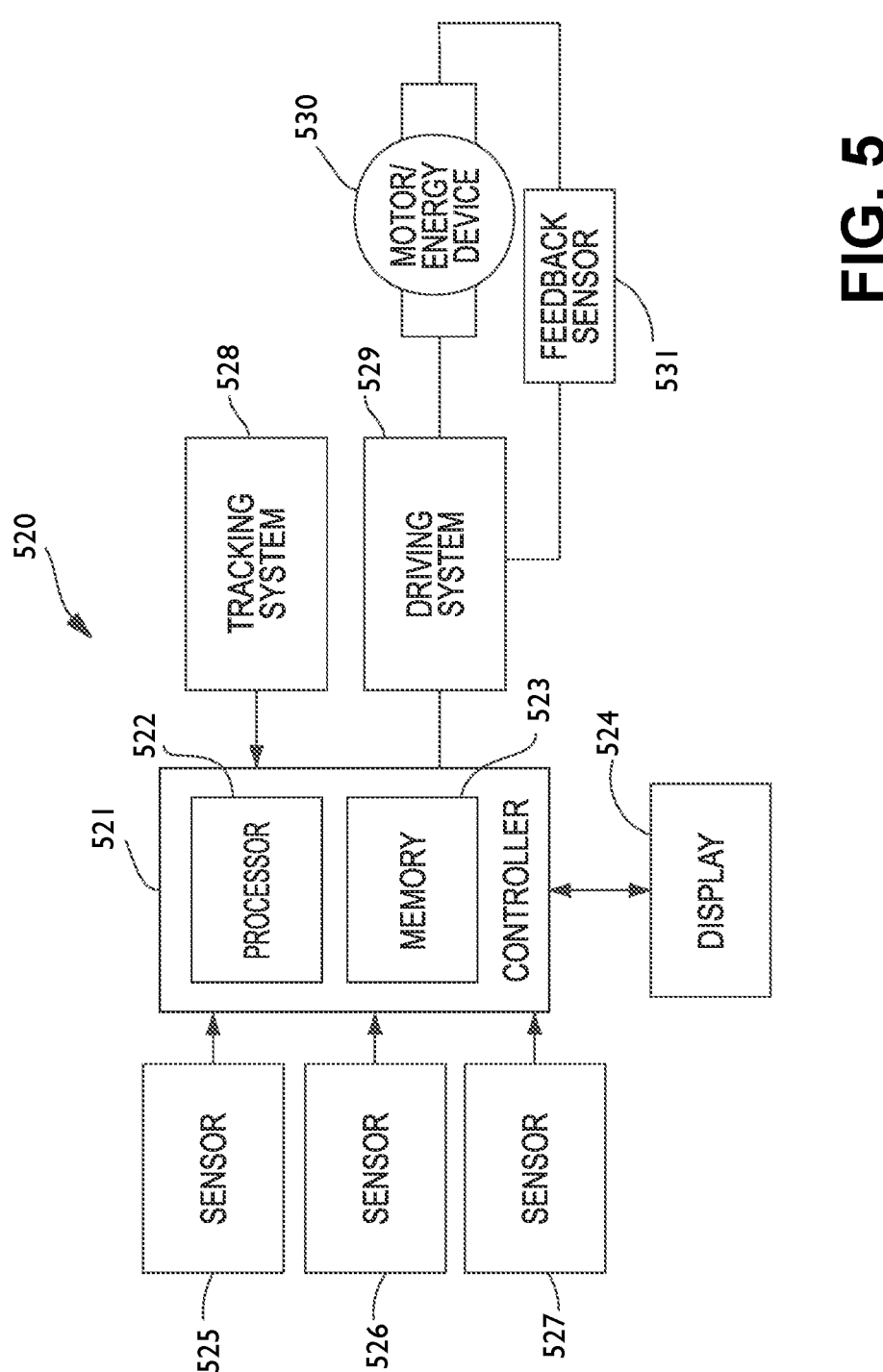
FIG. 5 illustrates a logic diagram of a control system of a surgical instrument.

FIG. 5 illustrates a logical diagram of a control system 520 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 520 may comprise a control circuit. The control circuit may include a microcontroller 521 comprising a processor 522 and a memory 523. One or more of sensors 525, 526, 527, for example, provide real-time feedback to the processor 522. A motor 530, driven by a motor driver 529, operably couples a longitudinally movable displacement member to drive the I-beam knife element. A tracking system 528 may be configured to determine the position of the longitudinally movable displacement member. The position information may be provided to the processor 522, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 524 may display a variety of operating conditions of the instruments and may include touch screen functionality for data input. Information displayed on the display 524 may be overlaid with images acquired via endoscopic imaging modules.

The microcontroller 521 may be any single-core or multicore processor such as those known under the trade name ARM Cortex by Texas Instruments. In one aspect, the main microcontroller 521 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with Stellaris WareR software, a 2 KB EEPROM, one or more PWM modules, one or more QEI analogs, and/or one or more 12-bit ADCs with 12 analog input channels, details of which are available for the product datasheet.

The microcontroller 521 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 521 may be programmed to perform various functions such as precise control over the speed and position of the knife and articulation systems. In one aspect, the microcontroller 521 may include a processor 522 and a memory 523. The electric motor 530 may be a brushed direct current (DC) motor with a gearbox and mechanical links to an articulation or knife system. In one aspect, a motor driver 529 may be an A3941 available from Allegro Microsystems, Inc. Other motor drivers may be readily substituted for use in the tracking system 528 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 521 may be programmed to provide precise control over the speed and position of displacement members and articulation systems. The microcontroller 521 may be configured to compute a response in the software of the microcontroller 521. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 530 may be controlled by the motor driver 529 and can be employed by the firing system of the surgical instrument or tool. In various forms, the motor 530 may be a brushed DC driving motor having a maximum rotational speed of approximately 25,000 RPM. In some examples, the motor 530 may include a brushless motor, a cordless motor, a synchronous motor, a stepper motor, or any other suitable electric motor. The motor driver 529 may comprise an H-bridge driver comprising field-effect transistors (FETs), for example. The motor 530 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 529 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 529 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 528 comprising an absolute positioning system.

The tracking system 528 may comprise a controlled motor drive circuit arrangement comprising a position sensor 525 according to one aspect of this disclosure. The position sensor 525 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 525 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 530 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 525 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 525 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 525 completing one or more revolutions for the full stroke of the displacement member. The position sensor 525 may complete multiple revolutions for the full stroke of the displacement member.

A series of switches, where n is an integer greater than one, may be employed alone or in combination with a gear reduction to provide a unique position signal for more than one revolution of the position sensor 525. The state of the switches may be fed back to the microcontroller 521 that applies logic to determine a unique position signal corresponding to the longitudinal linear displacement d1+d2+... dn of the displacement member. The output of the position sensor 525 is provided to the microcontroller 521. The position sensor 525 of the sensor arrangement may comprise a magnetic sensor, an analog rotary sensor like a potentiometer, or an array of analog Hall-effect elements, which output a unique combination of position signals or values.

The position sensor 525 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiberoptic, magneto-optic, and microelectromechanical systems-based magnetic sensors, among others.

The position sensor 525 for the tracking system 528 comprising an absolute positioning system may comprise a magnetic rotary absolute positioning system. The position sensor 525 may be implemented as an AS5055EQFT single-chip magnetic rotary position sensor available from Austria Microsystems, AG. The position sensor 525 is interfaced with the microcontroller 521 to provide an absolute positioning system. The position sensor 525 may be a low-voltage and low-power component and may include four Hall-effect elements in an area of the position sensor 525 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 521. The position sensor 525 may provide 12 or 14 bits of resolution. The position sensor 525 may be an AS5055 chip provided in a small QFN 16-pin 4×4×0.85 mm package.

The tracking system 528 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 525. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 530 has taken to infer the position of a device actuator, drive bar, knife, or the like.

A sensor 526, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 522. Alternatively, or in addition to the sensor 526, a sensor 527, such as, for example, a load sensor, can measure the closure force applied by the closure drive system to the anvil. The sensor 527, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 531 can be employed to measure the current drawn by the motor 530. The force required to advance the firing member can correspond to the current drawn by the motor 530, for example. The measured force may be converted to a digital signal and provided to the processor 522.

For example, the strain gauge sensor 526 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 526, such as, for example, a micro-strain gauge, that can be configured to measure one or more parameters of the end effector, for example. In one aspect, the strain gauge sensor 526 can measure the amplitude or magnitude of the strain exerted on a jaw member of an end effector during a clamping operation, which can be indicative of the tissue compression. The measured strain can be converted to a digital signal and provided to a processor 522 of the microcontroller 521. A load sensor 527 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 522.

The measurements of the tissue compression, the tissue thickness, and/or the force required to close the end effector on the tissue, as respectively measured by the sensors 526, 527, can be used by the microcontroller 521 to characterize the selected position of the firing member and/or the corresponding value of the speed of the firing member. In one instance, a memory 523 may store a technique, an equation, and/or a lookup table which can be employed by the microcontroller 521 in the assessment.

The control system 520 of the surgical instrument or tool also may comprise wired or wireless communication circuits to communicate with a surgical hub, such as surgical hub 460 for example, as shown in FIG. 4.

Figure 6:
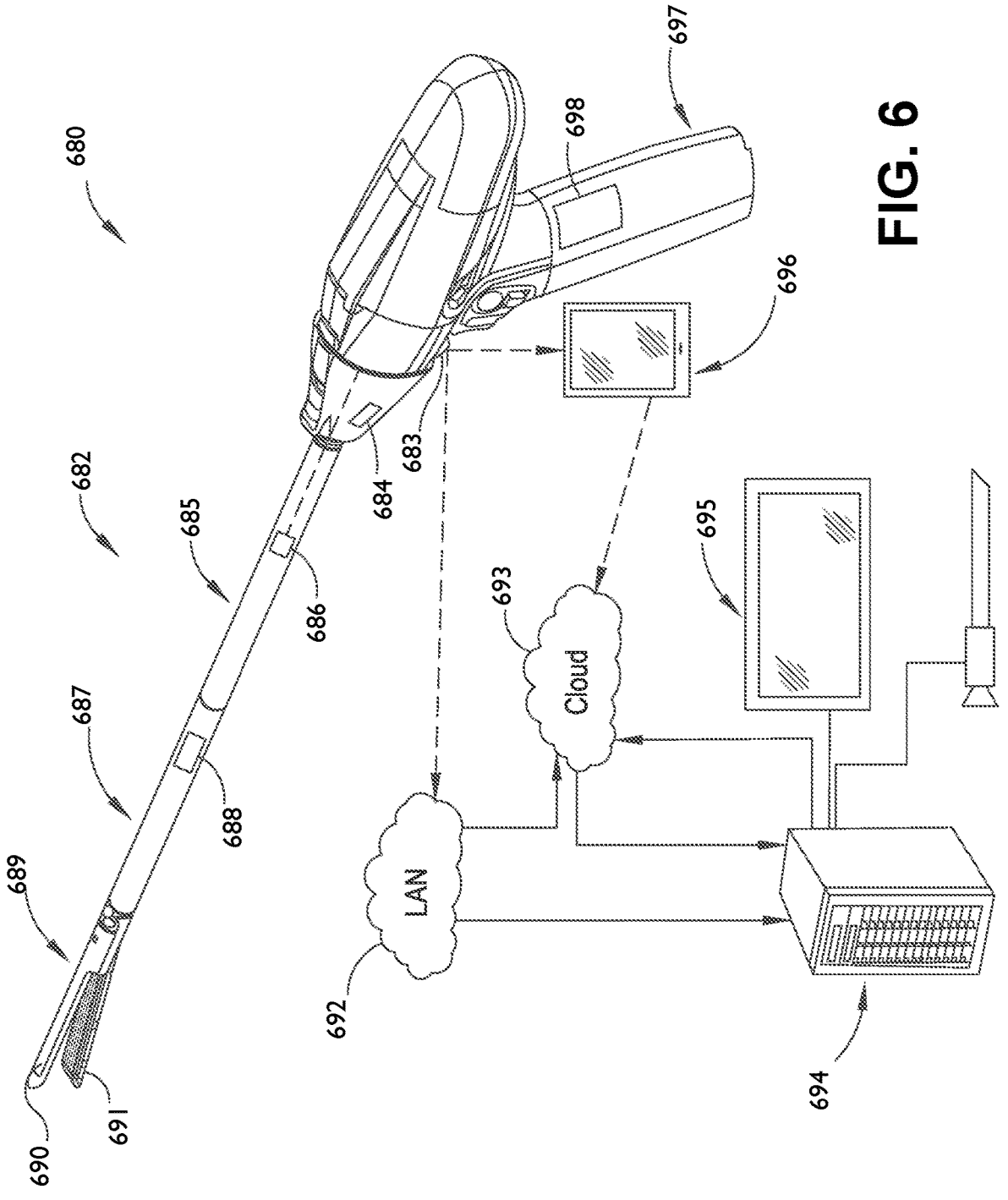
FIG. 6 shows an example surgical system that includes a handle having a controller and a motor, an adapter releasably coupled to the handle, and a loading unit releasably coupled to the adapter.

FIG. 6 illustrates an example surgical system 680 in accordance with the present disclosure and may include a surgical instrument 682 that can be in communication with a console 694 or a portable device 696 through a local area network 692 and/or a cloud network 693 via a wired and/or wireless connection. The console 694 and the portable device 696 may be any suitable computing device. The surgical instrument 682 may include a handle 697, an adapter 685, and a loading unit 687. The adapter 685 releasably couples to the handle 697 and the loading unit 687 releasably couples to the adapter 685 such that the adapter 685 transmits a force from a drive shaft to the loading unit 687. The adapter 685 or the loading unit 687 may include a force gauge (not explicitly shown) disposed therein to measure a force exerted on the loading unit 687. The loading unit 687 may include an end effector 689 having a first jaw 691 and a second jaw 690. The loading unit 687 may be an in-situ loaded or multi-firing loading unit (MFLU) that allows a clinician to fire a plurality of fasteners multiple times without requiring the loading unit 687 to be removed from a surgical site to reload the loading unit 687.

The first and second jaws 691, 690 may be configured to clamp tissue therebetween, fire fasteners through the clamped tissue, and sever the clamped tissue. The first jaw 691 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 690 may include an anvil that deforms or otherwise secures the fasteners, as the fasteners are ejected from the multi-fire fastener cartridge.

The handle 697 may include a motor that is coupled to the drive shaft to affect rotation of the drive shaft. The handle 697 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 697 may be in communication with a controller 698 of the handle 697 to selectively activate the motor to affect rotation of the drive shafts. The controller 698 may be disposed within the handle 697 and may be configured to receive input from the control interface and adapter data from the adapter 685 or loading unit data from the loading unit 687. The controller 698 may analyze the input from the control interface and the data received from the adapter 685 and/or loading unit 687 to selectively activate the motor. The handle 697 may also include a display that is viewable by a clinician during use of the handle 697. The display may be configured to display portions of the adapter or loading unit data before, during, or after firing of the instrument 682.

The adapter 685 may include an adapter identification device 684 disposed therein and the loading unit 687 may include a loading unit identification device 688 disposed therein. The adapter identification device 684 may be in communication with the controller 698, and the loading unit identification device 688 may be in communication with the controller 698. It will be appreciated that the loading unit identification device 688 may be in communication with the adapter identification device 684, which relays or passes communication from the loading unit identification device 688 to the controller 698.

The adapter 685 may also include a plurality of sensors 686 (one shown) disposed thereabout to detect various conditions of the adapter 685 or of the environment (e.g., if the adapter 685 is connected to a loading unit, if the adapter 685 is connected to a handle, if the drive shafts are rotating, the torque of the drive shafts, the strain of the drive shafts, the temperature within the adapter 685, a number of firings of the adapter 685, a peak force of the adapter 685 during firing, a total amount of force applied to the adapter 685, a peak retraction force of the adapter 685, a number of pauses of the adapter 685 during firing, etc.). The plurality of sensors 686 may provide an input to the adapter identification device 684 in the form of data signals. The data signals of the plurality of sensors 686 may be stored within or be used to update the adapter data stored within the adapter identification device 684. The data signals of the plurality of sensors 686 may be analog or digital. The plurality of sensors 686 may include a force gauge to measure a force exerted on the loading unit 687 during firing.

The handle 697 and the adapter 685 can be configured to interconnect the adapter identification device 684 and the loading unit identification device 688 with the controller 698 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 684 and the controller 698 may be in wireless communication with one another via a wireless connection separate from the electrical interface.

The handle 697 may include a transceiver 683 that is configured to transmit instrument data from the controller 698 to other components of the system 680 (e.g., the LAN 20292, the cloud 693, the console 694, or the portable device 696). The controller 698 may also transmit instrument data and/or measurement data associated with one or more sensors 686 to a surgical hub. The transceiver 683 may receive data (e.g., cartridge data, loading unit data, adapter data, or other notifications) from the surgical hub 670. The transceiver 683 may receive data (e.g., cartridge data, loading unit data, or adapter data) from the other components of the system 680. For example, the controller 698 may transmit instrument data including a serial number of an attached adapter (e.g., adapter 685) attached to the handle 697, a serial number of a loading unit (e.g., loading unit 687) attached to the adapter 685, and a serial number of a multi-fire fastener cartridge loaded into the loading unit to the console 694. Thereafter, the console 694 may transmit data (e.g., cartridge data, loading unit data, or adapter data) associated with the attached cartridge, loading unit, and adapter, respectively, back to the controller 698. The controller 698 can display messages on the local instrument display or transmit the message, via transceiver 683, to the console 694 or the portable device 696 to display the message on the display 695 or portable device screen, respectively.

Figure 7A:
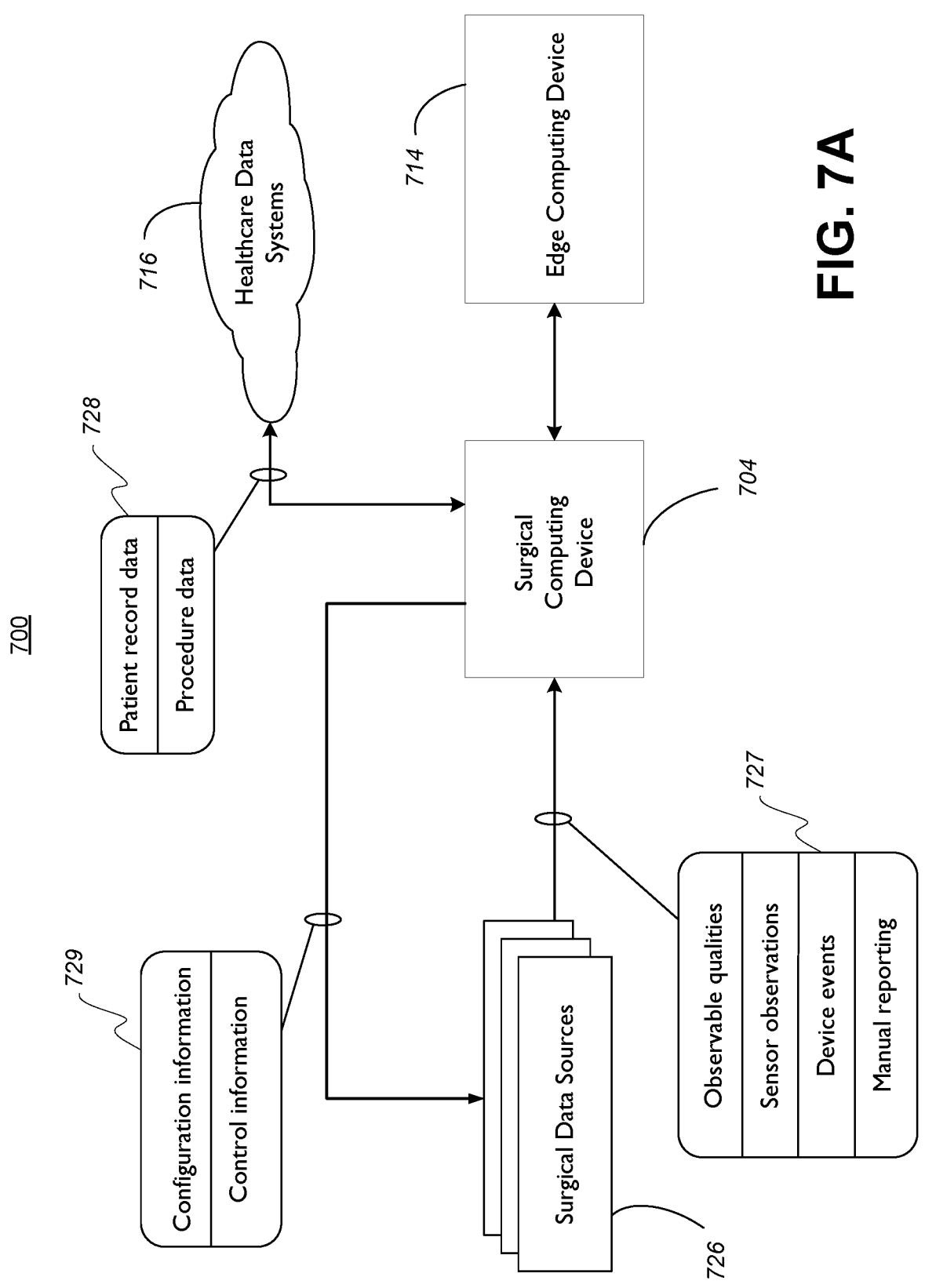
FIG. 7A-D show an example surgical system information matrix, an example information flow in a surgical system, an example information flow in a surgical system with a surgical robot, and an illustration of surgical information in the context of a procedure, respectively.

FIG. 7A illustrates a surgical system 700 that may include a matrix of surgical information. This surgical information may include any discrete atom of information relevant to surgical operation. Generally described, such surgical information may include information related to the context and scope of the surgery itself (e.g., healthcare information 728). Such information may include data such as procedure data and patient record data, for example. Procedure data and/or patient record data may be associated with a related healthcare data system 716 in communication with the surgical computing device 704.

The procedure data may include information related to the instruments and/or replaceable instrument components to be employed in a given procedure, such as a master list for example. The surgical computing device 704 may record (e.g., capture barcode scans) of the instruments and/or replaceable instrument components being put to use in the procedure. Such surgical information may be used to algorithmically confirm that appropriate configurations of surgical instruments and/or replaceable components are being used. See U.S. Patent Application Publication No. US 2020-0405296 A1 (U.S. patent application Ser. No. 16/458,103), titled PACKAGING FOR A REPLACEABLE COMPONENT OF A SURGICAL STAPLING SYSTEM, filed Jun. 30, 2019, the contents of which is hereby incorporated by reference herein in its entirety.

For example, patient record data may be suitable for use in changing the configurations of certain surgical devices. For example, patient data may be used to understand and improve surgical device algorithmic behavior. In an example, surgical staplers may adjust operational parameters related to compression, speed of operation, location of use, feedback based on information (e.g., information indicative of a specific patient's tissue and/or tissue characteristics) in the patient record. See U.S. Patent Application Publication No. US 2019-0200981 A1 (U.S. patent application Ser. No. 16/209,423), titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, the contents of which is hereby incorporated by reference herein in its entirety The surgical information may include information related to the configuration and/or control of devices being used in the surgery (e.g., device operational information 729). Such device operational information 729 may include information about the initial settings of surgical devices. Device operational information 729 may include information about changes to the settings of surgical devices. Device operational information 729 may include information about controls sent to the devices from the surgical computing device 704 and information flows related to such controls.

The surgical information may include information generated during the surgery itself (e.g., surgery information 727). Such surgery information 727 may be include any information generated by a surgical data source 726. The data sources 726 may include any device in a surgical context that may generate useful surgery information 727. This surgery information 727 may present itself as observable qualities of the data source 726. The observable qualities may include static qualities, such as a device's model number, serial number, and the like. The observable qualities may include dynamic qualities such as the state of configurable settings of the device. The surgery information 727 may present itself as the result of sensor observations for example. Sensor observations may include those from specific sensors within the surgical theatre, sensors for monitoring conditions, such as patient condition, sensors embedded in surgical devices, and the like. The sensor observations may include information used during the surgery, such as video, audio, and the like. The surgery information 727 may present itself as a device event data. Surgical devices may generate notifications and/or may log events, and such events may be included in surgery information 727 for communication to the surgical computing device 704. The surgery information 727 may present itself as the result of manual recording, for example. A healthcare professional may make a record during the surgery, such as asking that a note be taken, capturing a still image from a display, and the like The surgical data sources 726 may include modular devices (e.g., which can include sensors configured to detect parameters associated with the patient, HCPs and environment and/or the modular device itself), local databases (e.g., a local EMR database containing patient records), patient monitoring devices (e.g., a blood pressure (BP) monitor and an electrocardiogram monitor), HCP monitoring devices, environment monitoring devices, surgical instruments, surgical support equipment, and the like.

Intelligent surgical instruments may sense and measure certain operational parameters in the course of their operation. For example, intelligent surgical instruments, such as surgical robots, digital laparoscopic devices, and the like, may use such measurements to improve operation, for example to limit over compression, to reduce collateral damage, to minimize tissue tension, to optimize usage location, and the like. See U.S. Patent Application Publication No. US 2018-0049822 A1 (U.S. patent application Ser. No. 15/237,753), titled CONTROL OF ADVANCEMENT RATE AND APPLICATION FORCE BASED ON MEASURED FORCES, filed Aug. 16, 2016, the contents of which is hereby incorporated by reference herein in its entirety. Such surgical information may be communicated to the surgical computing device 704.

The surgical computing device 704 can be configured to derive the contextual information pertaining to the surgical procedure from the data based upon, for example, the particular combination(s) of received data or the particular order in which the data is received from the data sources 726. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical computing device 704 to derive or infer information related to the surgical procedure from received data can be referred to as "situational awareness." For example, the surgical computing device 704 can incorporate a situational awareness system, which is the hardware and/or programming associated with the surgical computing device 704 that derives contextual information pertaining to the surgical procedure from the received data and/or a surgical plan information received from the edge computing system 714 or a healthcare data system 716 (e.g., enterprise cloud server). Such situational awareness capabilities may be used to generation surgical information (such as control and/or configuration information) based on a sensed situation and/or usage. See U.S. Patent Application Publication No. US 2019-0104919 A1 (U.S. patent application Ser. No. 16/209, 478), titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018, the contents of which is hereby incorporated by reference herein in its entirety.

In operation, this matrix of surgical information may be present as one or more information flows. For example, surgical information may flow from the surgical data sources 726 to the surgical computing device 704. Surgical information may flow from the surgical computing device 704 to the surgical data sources 726 (e.g., surgical devices). Surgical information may flow between the surgical computing device 704 and one or more healthcare data systems 716. Surgical information may flow between the surgical computing device 704 and one or more edge computing devices 714. Aspects of the information flows, including, for example, information flow endpoints, information storage, data interpretation, and the like, may be managed relative to the surgical system 700 (e.g., relative to the healthcare facility) See U.S. Patent Application Publication No. US 2019-0206564 A1 (U.S. patent application Ser. No. 16/209, 490), titled METHOD FOR FACILITY DATA COLLECTION AND INTERPRETATION, filed Dec. 4, 2018, the contents of which is hereby incorporated by reference herein in its entirety.

Surgical information, as presented in its one or more information flows, may be used in connection with one or more artificial intelligence (AI) systems to further enhance the operation of the surgical system 700. For example, a machine learning system, such as that described herein, may operate on one or more information flows to further enhance the operation of the surgical system 700.

Figure 7B:
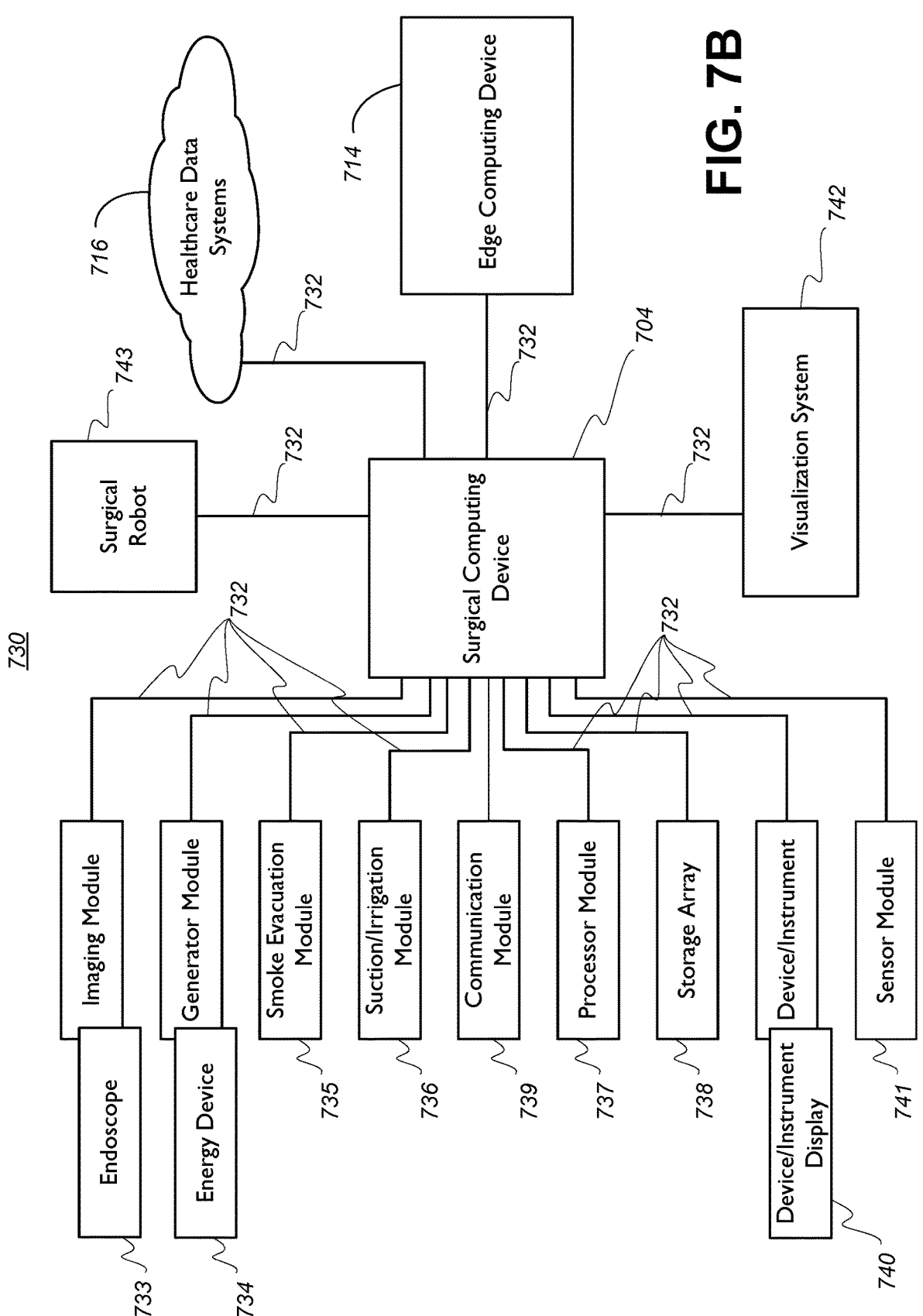

FIG. 7B shows an example computer-implement surgical system 730 with a plurality of information flows 732. A surgical computing device 704 may communication with and/or incorporate one or more surgical data sources. For example, an imaging module 733 (and endoscope) may exchange surgical information with the surgical computing device 704. Such information may include information from the imaging module 733 (and endoscope), such as video information, current settings, system status information, and the like. The imaging module 733 may receive information from the surgical computing device 704, such as control information, configuration information, operational updates (such as software/firmware), and the like.

For example, a generator module 734 (and corresponding energy device) may exchange surgical information with the surgical computing device 704. Such information may include information from the generator module 734 (and corresponding energy device), such as electrical information (e.g., current, voltage, impedance, frequency, wattage), activity state information, sensor information such as temperature, current settings, system events, active time duration, and activation timestamp, and the like. The generator module 734 may receive information from the surgical computing device 704, such as control information, configuration information, changes to the nature of the visible and audible notifications to the healthcare professional (e.g., changing the pitch, duration, and melody of audible tones), electrical application profiles and/or application logic that may instruct the generator module to provide energy with a defined characteristic curve over the application time, operational updates (such as software/firmware), and the like.

For example, a smoke evacuator 735 may exchange surgical information with the surgical computing device 704. Such information may include information from the smoke evacuator 735, such as operational information (e.g., revolutions per minute), activity state information, sensor information such as air temperature, current settings, system events, active time duration, and activation timestamp, and the like. The smoke evacuator 735 may receive information from the surgical computing device 704, such as control information, configuration information, operational updates (such as software/firmware), and the like.

For example, a suction/irrigation module 736 may exchange surgical information with the surgical computing device 704. Such information may include information from the suction/irrigation module 736, such as operational information (e.g., liters per minute), activity state information, internal sensor information, current settings, system events, active time duration, and activation timestamp, and the like. The suction/irrigation module 736 may receive information from the surgical computing device 704, such as control information, configuration information, operational updates (such as software/firmware), and the like.

For example, a communication module 739, a processor module 737, and/or a storage array 738 may exchange surgical information with the surgical computing device 704. In an example, the communication module 739, the processor module 737, and/or the storage array 738 may constitute all or part of the computing platform upon which the surgical computing device 704 runs. In an example, the communication module 739, the processor module 737, and/or the storage array 738 may provide local computing resources to other devices in the surgical system 730. Information from the communication module 739, the processor module 737, and/or the storage array 738 to the surgical computing device 704 may include logical computing-related reports, such as processing load, processing capacity, process identification, CPU %, CPU time, threads, GPU %, GPU time, memory utilization, memory thread, memory ports, energy usage, bandwidth related information, packets in, packets out, data rate, channel utilization, buffer status, packet loss information, system events, other state information, and the like. The communication module 739, the processor module 737, and/or the storage array 738 may receive information from the surgical computing device 704, such as control information, configuration information, operational updates (such as software/firmware), and the like. The communication module 739, the processor module 737, and/or the storage array 738 may also receive information from the surgical computing device 704 generated by another element or device of the surgical system 730. For example, data source information may be sent to and stored in the storage array. For example, data source information may be processed by the processor module 737.

For example, an intelligent instrument 740 (with or without a corresponding display) may exchange surgical information with the surgical computing device 704. Such information may include information from the intelligent instrument 740 relative to the instrument's operation, such as device electrical and/or mechanical information (e.g., current, voltage, impedance, frequency, wattage, torque, force, pressure, etc.), load state information (e.g., information regarding the identity, type, and/or status of reusables, such as staple cartridges), internal sensor information such as clamping force, tissue compression pressure and/or time, system events, active time duration, and activation timestamp, and the like. The intelligent instrument 740 may receive information from the surgical computing device 704, such as control information, configuration information, changes to the nature of the visible and audible notifications to the healthcare professional (e.g., changing the pitch, duration, and melody of audible tones), mechanical application profiles and/or application logic that may instruct a mechanical component of the instrument to operate with a defined characteristic (e.g., blade/anvil advance speed, mechanical advantage, firing time, etc.), operational updates (such as software/firmware), and the like.

For example, in a surgical stapling and cutting instrument, control and configuration information may be used to modify operational parameters, such as motor velocity for example. Data collections of surgical information may be used to define the power, force, and/or other functional operation and/or behavior of an intelligent surgical stapling and cutting instrument. See U.S. Pat. No. 10,881,399 B2 (U.S. patent application Ser. No. 15/628,175), titled TECHNIQUES FOR ADAPTIVE CONTROL OF MOTOR VELOCITY OF A SURGICAL STAPLING AND CUTTING INSTRUMENT, filed Jun. 20, 2017, the contents of which is hereby incorporated by reference herein in its entirety.

For example, in energy devices, control and configuration information (e.g., control and configuration information based on a situational awareness of the surgical computing device 704) may be used to adapt the function and/or behavior for improved results. See U.S. Patent Application Publication No. US 2019-0201047 A1 (U.S. patent application Ser. No. 16/209,458), titled METHOD FOR SMART ENERGY DEVICE INFRASTRUCTURE, filed Dec. 4, 2018, the contents of which is hereby incorporated by reference herein in its entirety. Likewise, in combo energy devices (e.g., devices which may use more than one energy modality) such control and/or configuration information may be used to select an appropriate operational mode. For example, the surgical computing device 704 may use surgical information including information being received from patient monitoring to send control and/or configuration information to the combo energy device. See U.S. Patent Application Publication No. US 2017-0202605 A1 (U.S. patent application Ser. No. 15/382,515), titled MODULAR BATTERY POWERED HANDHELD SURGICAL INSTRUMENT AND METHODS THEREFOR, filed Dec. 16, 2016, the contents of which is hereby incorporated by reference herein in its entirety.

For example, a sensor module 741 may exchange surgical information with the surgical computing device 704. Such information may include information from the sensor module 741 relative to its sensor function, such as sensor results themselves, observational frequency and/or resolution, observational type, device alerts such as alerts for sensor failure, observations exceeding a defined range, observations exceeding an observable range, and the like. The sensor module 741 may receive information from the surgical computing device 704, such as control information, configuration information, changes to the nature of observation (e.g., frequency, resolution, observational type etc.), triggers that define specific events for observation, on control, off control, data buffering, data preprocessing algorithms, operational updates (such as software/firmware), and the like.

For example, a visualization system 742 may exchange surgical information with the surgical computing device 704. Such information may include information from the visualization system 742, such visualization data itself (e.g., still image, video, advanced spectrum visualization, etc.), visualization metadata (e.g., visualization type, resolution, frame rate, encoding, bandwidth, etc.). The visualization system 742 may receive information from the surgical computing device 704, such as control information, configuration information, changes to the video settings (e.g., visualization type, resolution, frame rate, encoding, etc.), visual display overlay data, data buffering size, data preprocessing algorithms, operational updates (such as software/firmware), and the like.

Surgical information may be exchanged and/or used with advanced imaging systems. For example, surgical information may be exchanged and/or used to provide context for imaging data streams. For example, surgical information may be exchanged and/or used to expand the conditional understanding of such imaging data streams. See U.S. patent application Ser. No. 17/493,904, titled SURGICAL METHODS USING MULTI-SOURCE IMAGING, filed Oct. 5, 2021, the contents of which is hereby incorporated by reference herein in its entirety. See U.S. patent application Ser. No. 17/493,913, titled SURGICAL METHODS USING FIDUCIAL IDENTIFICATION AND TRACKING, filed Oct. 5, 2021, the contents of which is hereby incorporated by reference herein in its entirety.

For example, a surgical robot 743 may exchange surgical information with the surgical computing device 704. In an example, surgical information may include information related to the cooperative registration and interaction of surgical robotic systems. See U.S. patent application Ser. No. 17/449,765, titled COOPERATIVE ACCESS HYBRID PROCEDURES, filed Oct. 1, 2021, the contents of which is hereby incorporated by reference herein in its entirety. Information from the surgical robot 743 may include any aforementioned information as applied to robotic instruments, sensors, and devices. Information from the surgical robot 743 may also include information related to the robotic operation or control of such instruments, such as electrical/mechanical feedback of robot articulators, system events, system settings, mechanical resolution, control operation log, articulator path information, and the like. The surgical robot 743 may receive information from the surgical computing device 704, such as control information, configuration information, operational updates (such as software/firmware), and the like.

Surgical devices in communication with the surgical computing device 704 may exchange surgical information to aid in cooperative operation among the devices. For example, with the surgical robot 743 and the energy generator 734 may exchange surgical information with each other and/or the surgical computing device 704 for cooperative operation. Cooperative operation between the cooperatively the surgical robot 743 and the energy generator 734 may be used to minimize unwanted side effects like tissue sticking for example. Cooperative operation between the cooperatively the surgical robot 743 and the energy generator 734 may be used to improve tissue welding. See U.S. Patent Application Publication No. US 2019-0059929 A1 (U.S. patent application Ser. No. 15/689,072), titled METHODS, SYSTEMS, AND DEVICES FOR CONTROLLING ELECTROSURGICAL TOOLS, filed Aug. 29, 2017, the contents of which is hereby incorporated by reference herein in its entirety. Surgical information may be generated by the cooperating devices and/or the surgical computing device 704 in connection with their cooperative operation.

The surgical computing system 704 may be record, analyze, and/or act on surgical information flows, like those disclosed above for example. The surgical computing system 704 may aggregate such data for analysis. For example, the surgical computing system 704 may perform operations such as defining device relationships, establishing device cooperative behavior, monitoring and/or storing procedure details, and the like. Surgical information related to such operations may be further analyzed to refine algorithms, identify trends, and/or adapt surgical procedures. For example, surgical information may be further analyzed in comparison with patient outcomes as a function of such operations. See U.S. Patent Application Publication No. US 2019-0206562 A1 (U.S. patent application Ser. No. 16/209, 416), titled METHOD OF HUB COMMUNICATION, PROCESSING, DISPLAY, AND CLOUD ANALYTICS, filed Dec. 4, 2018, the contents of which is hereby incorporated by reference herein in its entirety.

Figure 7C:
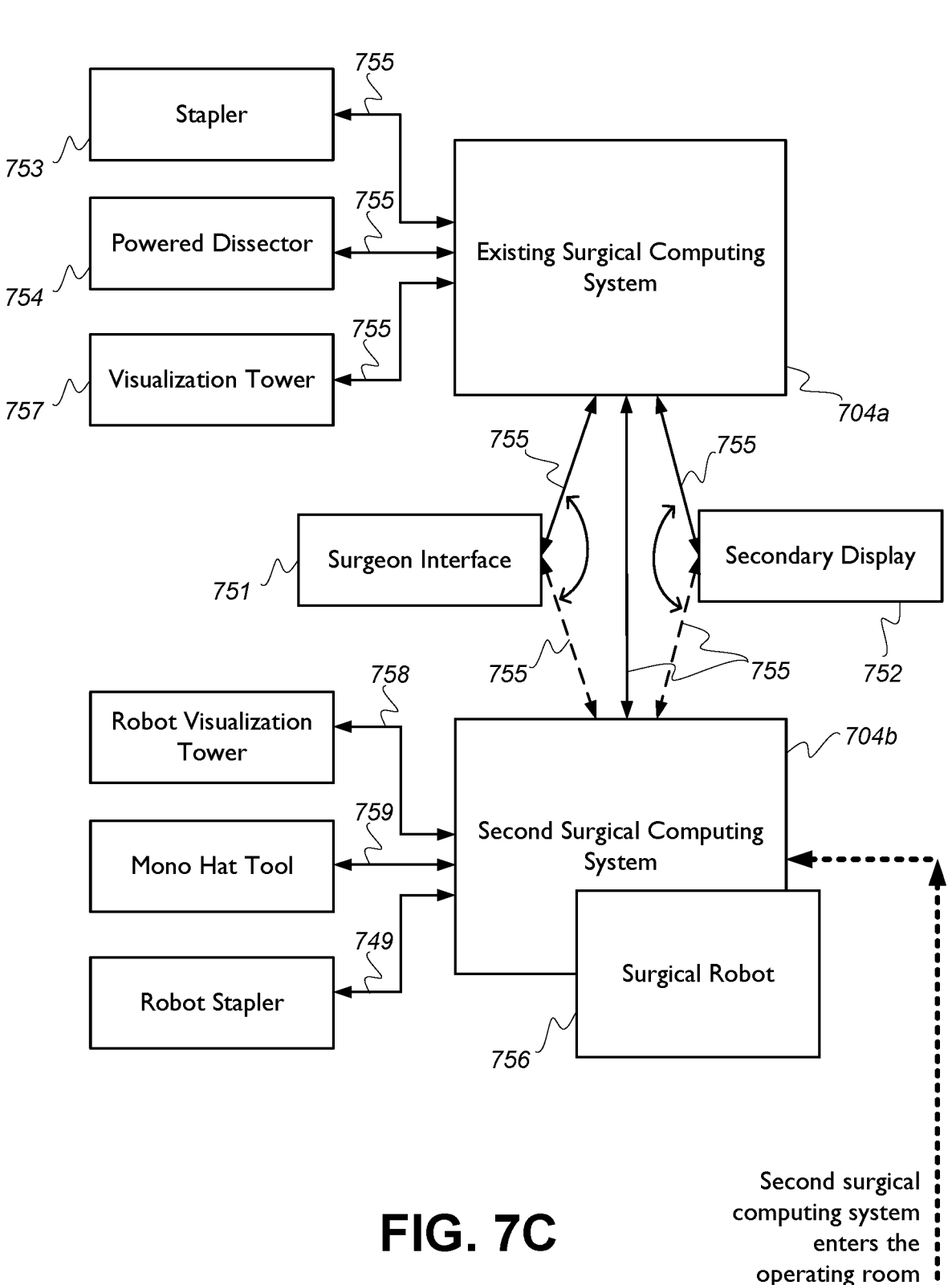

FIG. 7C illustrates an example information flow associated with a plurality of surgical computing systems 704a, 704b in a common environment. When the overall configuration of a computer-implement surgical system (e.g., computer-implement surgical system 750) changes (e.g., when data sources are added and/or removed from the surgical computing system, for example), further surgical information may be generated to reflect the changes. In this example, a second surgical computing system 704b (e.g., surgical hub) may be added (with a corresponding surgical robot) to surgical system 750 with an existing surgical computing system 704a. The messaging flow described here represents further surgical information flows 755 to be employed as disclosed herein (e.g., further consolidated, analyzed, and/or processed according to an algorithm, such as a machine learning algorithm).

Here, the two surgical computing systems 704a, 704b request permission from a surgical operator for the second surgical computing system 704b (with the corresponding surgical robot 756) to take control of the operating room from the existing surgical computing system 704a. The second surgical computing system 704b presents in the operating theater with control of the corresponding surgical robot 756, a robot visualization tower 758, a mono hat tool 759, and a robot stapler 749. The permission can be requested through a surgeon interface or console 751. Once permission is granted, the second surgical computing system 704b messages the existing surgical computing system 704a a request a transfer of control of the operating room.

In an example, the surgical computing systems 704a, 704b can negotiate the nature of their interaction without external input based on previously gathered data. For example, the surgical computing systems 704a, 704b may collectively determine that the next surgical task requires use of a robotic system. Such determination may cause the existing surgical computing system 704a to autonomously surrender control of the operating room to the second surgical computing system 704b. Upon completion of the surgical task, the second surgical computing system 704*b* may then autonomously return the control of the operating room to the existing surgical computing system 704*a*.

As illustrated in FIG. 7C, the existing surgical computing system 704*a* has transferred control to the second surgical computing system 704*b*, which has also taken control of the surgeon interface 751 and the secondary display 752. The second surgical computing system 704*b* assigns new identification numbers to the newly transferred devices. The existing surgical computing system 704*a* retains control the handheld stapler 753, the handheld powered dissector 754, and visualization tower 757. In addition, the existing surgical computing system 704*a* may perform a supporting role, wherein the processing and storage capabilities of the existing surgical computing system 704*a* are now available to the second surgical computing system 704*b*.

Figure 7D:
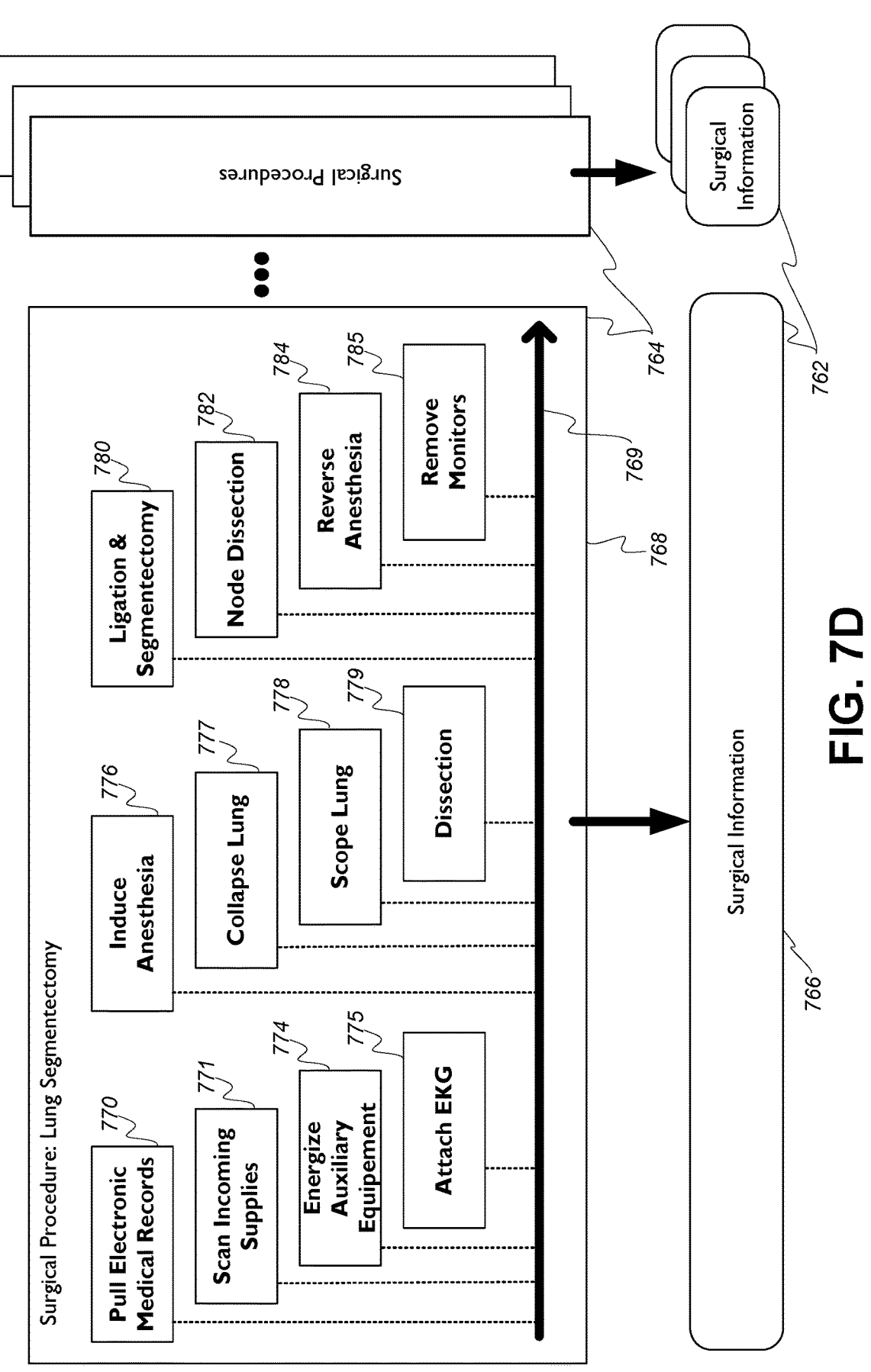

FIG. 7D illustrates an example surgical information flow in the context of a surgical procedure and a corresponding example use of the surgical information for predictive modeling. The surgical information disclosed herein may provide data regarding one or more surgical procedures, including the surgical tasks, instruments, instrument settings, operational information, procedural variations, and corresponding desirable metrics, such as improved patient outcomes, lower cost (e.g., fewer resources utilized, less surgical time, etc.). The surgical information disclosed herein (e.g., that disclosed in regard to FIGS. 7A-C) in the context of one or more surgical systems and devices disclosed herein, provides a platform upon which the specific machine learning algorithms and techniques disclosed herein may be used.

Surgical information 762 from a plurality of surgical procedures 764 (e.g., a subset of surgical information from each procedure) may be collected. The surgical information 762 may be collected from the plurality of surgical procedures 764 by collecting data represented by the one or more information flows disclosed herein, for example.

To illustrate, example instance of surgical information 766 may be generated from the example procedure 768 (e.g, a lung segmentectomy procedure as shown on a timeline 769). Surgical information 766 may be generated during the preoperative planning and may include patient record information. Surgical information 766 may be generated from the data sources (e.g., data sources 726) during the course of the surgical procedure, including data generated each time medical personnel utilize a modular device that is paired with the surgical computing system (e.g., surgical computing system 704). The surgical computing system may receive this data from the paired modular devices and other data sources The surgical computing system itself may generate surgical information as part of its operation during the procedure. For example, the surgical computing system may record information relating to configuration and control operations. The surgical computing system may record information related to situational awareness activities. For example, the surgical computing system may record the recommendations, prompts, and/or other information provided to the heathcare team (e.g., provided via a display screen) that may be pertinent for the next procedural step. For example, the surgical computing system may record configuration and control changes (e.g., the adjusting of modular devices based on the context). Such configuration and control changes may include activating monitors, adjusting the field of view (FOV) of a medical imaging device, changing the energy level of an ultrasonic surgical instrument or RF electrosurgical instrument, or the like.

At 770, the hospital staff members retrieve the patient's EMR from the hospital's EMR database. Based on select patient data in the EMR, the surgical computing system determines that the procedure to be performed is a thoracic procedure.

At 771, the staff members scan the incoming medical supplies for the procedure. The surgical computing system may cross-reference the scanned supplies with a list of supplies that are utilized in various types of procedures. The surgical computing system may confirm that the mix of supplies corresponds to a thoracic procedure. Further, the surgical computing system may determine that the procedure is not a wedge procedure (because the incoming supplies either lack certain supplies that are necessary for a thoracic wedge procedure or do not otherwise correspond to a thoracic wedge procedure). The medical personnel may also scan the patient band via a scanner that is communicably connected to the surgical computing system. The surgical computing system may confirm the patient's identity based on the scanned data.

At 774, the medical staff turns on the auxiliary equipment. The auxiliary equipment being utilized can vary according to the type of surgical procedure and the techniques to be used by the surgeon. In this example, the auxiliary equipment may include a smoke evacuator, an insufflator, and medical imaging device. When activated, the auxiliary equipment may pair with the surgical computing system. The surgical computing system may derive contextual information about the surgical procedure based on the types of paired. In this example, the surgical computing system determines that the surgical procedure is a VATS procedure based on this particular combination of paired devices. The contextual information about the surgical procedure may be confirmed by the surgical computing system via information from the patient's EMR.

The surgical computing system may retrieve the steps of the procedure to be performed. For example, the steps may be associated with a procedural plan (e.g., a procedural plan specific to this patient's surgery, a procedural plan associated with a particular surgeon, a procedural plan template for the procedure generally, or the like).

At 775, the staff members attach the EKG electrodes and other patient monitoring devices to the patient. The EKG electrodes and other patient monitoring devices pair with the surgical computing system. The surgical computing system may receive data from the patient monitoring devices.

At 776, the medical personnel induce anesthesia in the patient. The surgical computing system may record information related to this procedural step such as data from the modular devices and/or patient monitoring devices, including EKG data, blood pressure data, ventilator data, or combinations thereof, for example.

At 777, the patient's lung subject to operation is collapsed (ventilation may be switched to the contralateral lung). The surgical computing system may determine that this procedural step has commenced and may collect surgical information accordingly, including for example, ventilator data, one or more timestamps, and the like At 778, the medical imaging device (e.g., a scope) is inserted and video from the medical imaging device is initiated. The surgical computing system may receive the medical imaging device data (i.e., video or image data) through its connection to the medical imaging device. The data from the medical imaging device may include imaging data and/or imaging metadata, such as the angle at which the medical imaging device is oriented with respect to the visualization of the patient's anatomy, the number or medical imaging devices presently active, and the like. The surgical computing system may record positioning information of the medical imaging device. For example, one technique for performing a VATS lobectomy places the camera in the lower anterior corner of the patient's chest cavity above the diaphragm. Another technique for performing a VATS segmentectomy places the camera in an anterior intercostal position relative to the segmental fissure.)

Using pattern recognition or machine learning techniques, for example, the surgical computing system may be trained to recognize the positioning of the medical imaging device according to the visualization of the patient's anatomy. For example, one technique for performing a VATS lobectomy utilizes a single medical imaging device. Another technique for performing a VATS segmentectomy uses multiple cameras. Yet another technique for performing a VATS segmentectomy uses an infrared light source (which may be communicably coupled to the surgical computing system as part of the visualization system).

At 779, the surgical team begins the dissection step of the procedure. The surgical computing system may collect data from the RF or ultrasonic generator indicating that an energy instrument is being fired. The surgical computing system may cross-reference the received data with the retrieved steps of the surgical procedure to determine that an energy instrument being fired at this point in the process (i.e., after the completion of the previously discussed steps of the procedure) corresponds to the dissection step. In an example, the energy instrument may be an energy tool mounted to a robotic arm of a robotic surgical system.

At 780, the surgical team proceeds to the ligation step of the procedure. The surgical computing system may collect surgical information 766 with regard to the surgeon ligating arteries and veins based on receiving data from the surgical stapling and cutting instrument indicating that such instrument is being fired. Next, the segmentectomy portion of the procedure is performed. The surgical computing system may collect information relating to the surgeon transecting the parenchyma. For example, the surgical computing system may receive surgical information 766 from the surgical stapling and cutting instrument, including data regarding its cartridge, settings, firing details, and the like.

At 782, the node dissection step is then performed. The surgical computing system may collect surgical information 766 with regard to the surgical team dissecting the node and performing a leak test. For example, the surgical computing system may collect data received from the generator indicating that an RF or ultrasonic instrument is being fired and including the electrical and status information associated with the firing. Surgeons regularly switch back and forth between surgical stapling/cutting instruments and surgical energy (i.e., RF or ultrasonic) instruments depending upon the particular step in the procedure. The surgical computing system may collect surgical information 766 in view of the particular sequence in which the stapling/cutting instruments and surgical energy instruments are used. In an example, robotic tools may be used for one or more steps in a surgical procedure. The surgeon may alternate between robotic tools and handheld surgical instruments and/or can use the devices concurrently, for example.

Next, the incisions are closed up and the post-operative portion of the procedure begins. At 784, the patient's anesthesia is reversed. The surgical computing system may collect surgical information regarding the patient emerging from the anesthesia based on ventilator data (e.g., the patient's breathing rate begins increasing), for example.

At 785, the medical personnel remove the various patient monitoring devices from the patient. The surgical computing system may collect information regarding the conclusion of the procedure. For example, the surgical computing system may collect information related to the loss of EKG, BP, and other data from the patient monitoring devices.

The surgical information 762 (including the surgical information 766) may be structured and/or labeled. The surgical computing system may provide such structure and/or labeling inherently in the data collection. For example, in surgical information 762 may be labeled according to a particular characteristic, a desired result (e.g., efficiency, patient outcome, cost, and/or a combination of the same, or the like), a certain surgical technique, an aspect of instrument use (e.g., selection, timing, and activation of a surgical instrument, the instrument's settings, the nature of the instrument's use, etc.), the identity of the health care professionals involved, a specific patient characteristic, or the like, each of which may be present in the data collection.

Surgical information (e.g., surgical information 762 collected across procedures 764) may be used in connection with one or more artificial intelligence (AI) systems. AI may be used to perform computer cognitive tasks. For example, AI may be used to perform complex tasks based on observations of data. AI may be used to enable computing systems to perform cognitive tasks and solve complex tasks. AI may include using machine learning and machine learning techniques. ML techniques may include performing complex tasks, for example, without being programmed (e.g., explicitly programmed). For example, a ML technique may improve over time based on completing tasks with different inputs. A ML process may train itself, for example using input data and/or a learning dataset.

Machine learning (ML) techniques may be employed, for example, in the medical field. For example, ML may be used on a set of data (e.g., a set of surgical data) to produce an output (e.g., reduced surgical data, processed surgical data). In examples, the output of a ML process may include identified trends or relationships of the data that were input for processing. The outputs may include verifying results and/or conclusions associated with the input data. In examples, an input to a ML process may include medical data, such as surgical images and patient scans. The ML process may output a determined medical condition based on the input surgical images and patient scans. The ML process may be used to diagnose medical conditions, for example, based on the surgical scans.

ML processes may improve themselves, for example, using the historic data that trained the ML processes and/or the input data. Therefore, ML processes may be constantly improving with added inputs and processing. The ML processes may update based on input data. For example, over time, a ML process that produces medical conclusions based on medical data may improve and become more accurate and consistent in medical diagnoses.

ML processes may be used to solve different complex tasks (e.g., medical tasks). For example, ML processes may be used for data reduction, data preparation, data processing, trend identification, conclusion determination, medical diagnoses, and/or the like. For example, ML processes may take in surgical data as an input and process the data to be used for medical analysis. The processed data may be used to determine a medical diagnosis. In the end, the ML processes may take raw surgical data and generate useful medical information (e.g., medical trends and/or diagnoses) associated with the raw surgical data.

ML processes may be combined to perform different discrete tasks on an input data set. For example, a ML process may include testing different combinations of ML sub-processes performing discrete tasks to determine which combination of ML sub-processes performs the best (e.g., competitive usage of different process/algorithm types and training to determine the best combination for a dataset). For example, the ML process may include sub-process (e.g., algorithm) control and monitoring to improve and/or verify results and/or conclusions (e.g., error bounding).

A ML process may be initialized and/or setup to perform tasks. For example, the ML process may be initialized based on initialization configuration information. The initialized ML process may be untrained and/or a base ML process for performing the task. The untrained ML process may be inaccurate in performing the designated tasks. As the ML process becomes trained, the tasks may be performed more accurately.

The initialization configuration information for a ML process may include initial settings and/or parameters. For example, the initial settings and/or parameters may include defined ranges for the ML process to employ. The ranges may include ranges for manual inputs and/or received data. The ranges may include default ranges and/or randomized ranges for variables not received, for example, which may be used to complete a dataset for processing. For example, if a dataset is missing a data range, the default data range may be used as a substitute to perform the ML process.

The initialization configuration information for a ML process may include data storage locations. For example, locations or data storages and/or databases associated with data interactions may be included. The databases associated with data interactions may be used to identify trends in datasets. The databases associated with data interactions may include mappings of data to a medical condition. For example, a database associated with data interactions may include a mapping for heart rate data to medical conditions, such as, for example, arrythmia and/or the like.

The initialization configuration information may include parameters associated with defining the system. The initialization configuration information may include instructions (e.g., methods) associated with displaying, confirming, and/or providing information to a user. For example, the initialization configuration may include instructions to the ML process to output the data in a specific format for visualization for a user.

ML techniques may be used, for example, to perform data reduction. ML techniques for data reductions may include using multiple different data reduction techniques. For example, ML techniques for data reductions may include using one or more of the following: CUR matrix decomposition; a decision tree; expectation-maximization (EM) processes (e.g., algorithms); explicit semantic analysis (ESA); exponential smoothing forecast; generalized linear model; k-means clustering (e.g., nearest neighbor); Naive Bayes; neural network processes; a multivariate analysis; an o-cluster; a singular value decomposition; Q-learning; a temporal difference (TD); deep adversarial networks; support vector machines (SVM); linear regression; reducing dimensionality; linear discriminant analysis (LDA); adaptive boosting (e.g., AdaBoost); gradient descent (e.g., Stochastic gradient descent (SGD)); outlier detection; and/or the like.

ML techniques may be used to perform data reduction, for example, using CUR matrix decompositions. A CUR matrix decomposition may include using a matrix decomposition model (e.g., process, algorithm), such as a low-rank matrix decomposition model. For example, CUR matrix decomposition may include a low-rank matrix decomposition process that is expressed (e.g., explicitly expressed) in a number (e.g., small number) of columns and/or rows of a data matrix (e.g., the CUR matrix decomposition may be interpretable). CUR matrix decomposition may include selecting columns and/or rows associated with statistical leverage and/or a large influence in the data matrix. Using CUR matrix decomposition may enable identification of attributes and/or rows in the data matrix. The simplification of a larger dataset (e.g., using CUR matrix decomposition) may enable review and interaction (e.g., with the data) by a user. CUR matrix decomposition may facilitate regression, classification, clustering, and/or the like.

ML techniques may be used to perform data reduction, for example, using decision trees (e.g., decision tree model). Decision trees may be used, for example, as a framework to quantify values of outcomes and/or the probabilities of outcomes occurring. Decision trees may be used, for example, to calculate the value of uncertain outcome nodes (e.g., in a decision tree). Decision trees may be used, for example, to calculate the value of decision nodes (e.g., in a decision tree). A decision tree may be a model to enable classification and/or regression (e.g., adaptable to classification and/or regression problems). Decision trees may be used to analyze numerical (e.g., continuous values) and/or categorical data. Decision trees may be more successful with large data sets and/or may be more efficient (e.g., as compared to other data reduction techniques).

Decision trees may be used in combination with other decision trees. For example, a random forest may refer to a collection of decision trees (e.g., ensemble of decision trees). A random forest may include a collection of decision trees whose results may be aggregated into a result. A random forest may be a supervised learning algorithm. A random forest may be trained, for example, using a bagging training process.

A random decision forest (e.g., random forest) may add randomness (e.g., additional randomness) to a model, for example, while growing the trees. A random forest may be used to search for a best feature among a random subset of features, for example, rather than searching for the most important feature (e.g., while splitting a node). Searching for the best feature among a random subset of features may result in a wide diversity that may result in a better (e.g., more efficient and/or accurate) model.

A random forest may include using parallel ensembling. Parallel ensembling may include fitting (e.g., several) decision tree classifiers in parallel, for example, on different data set sub-samples. Parallel ensembling may include using majority voting or averages for outcomes or final results. Parallel ensembling may be used to minimize overfitting and/or increase prediction accuracy and control. A random forest with multiple decision trees may (e.g., generally) be more accurate than a single decision tree-based model. A series of decision trees with controlled variation may be built, for example, by combining bootstrap aggregation (e.g., bagging) and random feature selection.

ML techniques may be used to perform data reduction, for example, using an expectation maximization (EM) model (e.g., process, algorithm). For example, an EM model may be used to find a likelihood (e.g., local maximum likelihood) parameter of a statistical model. An EM model may be used for cases where equations may not be solved directly. An EM model may consider latent variables and/or unknown parameters and known data observations. For example, the EM model may determine that missing values exist in a data set. The EM model receive configuration information indicating to assume the existence of missing (e.g., unobserved) data points in a data set.

An EM model may use component clustering. For example, component clustering may enable the grouping of EM components into high-level clusters. Components may be treated as clustered, for example, if component clustering is disabled (e.g., in an EM model).

ML techniques may be used to perform data reduction, for example, using explicit semantic analysis (ESA). ESA may be used at a level of semantics (e.g., meaning) rather than on vocabulary (e.g., surface form vocabulary) of words or a document. ESA may focus on the meaning of a set of text, for example, as a combination of the concepts found in the text. ESA may be used in document classification. ESA may be used for a semantic relatedness calculation (e.g., how similar in meaning words or pieces of text are to each other). ESA may be used for information retrieval.

ESA may be used in document classification, for example. Document classification may include tagging documents for managing and sorting. Tagging a document (e.g., with a keyword) may allow for easier searching. Keyword tagging (e.g., only using keyword tagging) may limit the accuracy and/or efficiency of document classification. For example, using keyword tagging may uncover (e.g., only uncover) documents with the keywords and not documents with words with similar meaning to the keywords. Classifying text semantically (e.g., using ESA) may improve a model's understanding of text. Classifying text semantically may include representing documents as concepts and lowering dependence on specific keywords.

ML techniques may be used to perform data reduction, for example, using an exponential smoothing forecast model. Exponential smoothing may be used to smooth time series data, for example, using an exponential window function. For example, in a moving average, past observations may be weighted equally, but exponential functions may be used to assign exponentially decreasing weights over time.

ML techniques may be used to perform data reduction, for example, using linear regression. Linear regression may be used to predict continuous outcomes. For example, linear regression may be used to predict the value of a variable (e.g., dependent variable) based on the value of a different variable (e.g., independent variable). Linear regression may apply a linear approach for modeling a relationship between a scalar response and one or more explanatory variables (e.g., dependent and/or independent variables). Simple linear regression may refer to linear regression use cases associated with one explanatory variable. Multiple linear regression may refer to linear regression use cases associated with more than one explanatory variables. Linear regression may model relationships, for example, using linear predictor functions. The linear predictor functions may estimate unknown model parameters from a data set.

For example, linear regression may be used to identify patterns within a training dataset. The identified patterns may relate to values and/or label groupings. The model may learn a relationship between the (e.g., each) label and the expected outcomes. After training, the model may be used on raw data outside the training data set (e.g., data without a mapped and/or known output). The trained model using linear regression may determine calculated predictions associated with the raw data, for example, such as identifying seasonal changes in sales data.

ML techniques may be used to perform data reduction, for example, a generalized linear model (GLM). A GLM may be used as a flexible generalization of linear regression. GLM may generalize linear regression, for example, by enabling a linear model to be related to a response variable.

ML techniques may be used to perform data reduction, for example, using k-means clustering (e.g., a nearest neighbor model). K-means clustering may be used for vector quantization. K-means clustering may be used in signal processing. K-means clustering may be aimed at partitioning n observations into k clusters, for example, where each observation is classified into a cluster with the closest mean.

K-means clustering may include K-Nearest Neighbors (KNN) learning. KNN may be an instance-based learning (e.g., non-generalized learning, lazy learning). KNN may refrain from constructing a general internal model. KNN may include storing instances corresponding to training data in an n-dimensional space. KNN may use data and classify data points, for example, based on similarity measures (e.g., Euclidean distance function). Classification may be computed, for example, based on a majority vote of the k nearest neighbors of a (e.g., each) point. KNN may be robust for noisy training data. Accuracy may depend on data quality (e.g., for KNN). KNN may include choosing a number of neighbors to be considered (e.g., optimal number of neighbors to be considered). KNN may be used for classification and/or regression.

ML techniques may be used to perform data reduction, for example, using a Naive Bayes model (e.g., process). A Naive Bayes model may be used, for example, to construct classifiers. A Naive Bayes model may be used to assign class labels to problem instances (e.g., represented as vectors of feature values). The class labels may be drawn from a set (e.g., finite set). Different processes (e.g., algorithms) may be used to train the classifiers. A family of processes (e.g., family of algorithms) may be used. The family of processes may be based on a principle where the Naive Bayes classifiers (e.g., all the Naive Bayes) classifiers assume that the value of a feature is independent of the value of a different feature (e.g., given the class variable).

ML techniques may be used to perform data reduction, for example, using a neural network. Neural networks may learn (e.g., be trained) by processing examples, for example, to perform other tasks (e.g., similar tasks). A processing example may include an input and a result (e.g., input mapped to a result). The neural network may learn by forming probability-weighted associations between the input and the result. The probability-weighted associations may be stored within a data structure of the neural network. The training of the neural network from a given example may be conducted by determining the difference between a processed output of the network (e.g., prediction) and a target output. The difference may be the error. The neural network may adjust the weighted associations (e.g., stored weighted associations), for example, according to a learning rule and the error value.

ML techniques may be used to perform data reduction, for example, using multivariate analysis. Multivariate analysis may include performing multivariate state estimation and/or non-negative matrix factorization.

ML techniques may be used to perform data reduction, for example, using support vector machines (SVMs). SVMs may be used in a multi-dimensional space (e.g., high-dimensional space, infinite-dimensional space). SVCs may be used to construct a hyper-plane (e.g., set of hyper-planes). A hyper-plane that has the greatest distance (e.g., compared to the other constructed hyper-planes) from a nearest training data point in a class (e.g., any class) may achieve a strong separation (e.g., in general, the greater the margin, the lower the classifier's generalization error). SVMs may be effective in high-dimensional spaces. SVMs may behave differently, for example, based on different mathematical functions (e.g., the kernel, kernel functions). For example, kernel functions may include one or more of the following: linear, polynomial, radial basis function (RBF), sigmoid, etc. The kernel functions may be used as a SVM classifier. SVM may be limited in use cases, for example, where a data set contains high amounts of noise (e.g., overlapping target classes).

ML techniques may be used to perform data reduction, for example, such as reducing dimensionality. Reducing dimensionality of a sample of data (e.g., unlabeled data) may help refine groups and/or clusters. Reducing a number of variables in a model may simplify data trends. Simplified data trends may enable more efficient processing. Reducing dimensionality may be used, for example, if many (e.g., too many) dimensions are clouding (e.g., negatively affecting) insights, trends, patterns, conclusions, and/or the like.

Reducing dimensionality may include using principal component analysis (PCA). PCA may be used to establish principal components that govern a relationship between data points. PCA may focus on simplifying (e.g., only simplifying) the principal components. Reducing dimensionality (e.g., PCA) may be used to maintain the variety of data grouping in a data set, but streamline the number of separate groups.

ML techniques may be used to perform data reduction, for example, linear discriminant analysis (LDA). LDA may refer to a linear decision boundary classifier, for example, that may be created by fitting class conditional densities to data (e.g., and applying Bayes' rule). LDA may include a generalization of Fisher's linear discriminant (e.g., projecting a given dataset into lower-dimensional space, for example, to reduce dimensionality and minimize complexity of a model and reduce computational costs). An LDA model (e.g., standard LDA model) may suit a class with a Gaussian density. The LDA model may assume that the classes (e.g., all clases) share a covariance matrix. LDA may be similar to analysis of variance (ANOVA) processes and/or regression analysis. For example, LDA may be used to express a dependent variable as a linear combination of other features and/or measurements.

ML techniques may be used to perform data reduction, for example, such as adaptive boosting (e.g., AdaBoost). Adaptive boosting may include creating a classifier (e.g., powerful classifier). Adaptive boosting may include creating a classier by combining multiple classifiers (e.g., poorly performing classifiers), for example, to obtain a resulting classifier with high accuracy. AdaBoost may be an adaptive classifier that improves the efficiency of a classifier. AdaBoost may trigger overfits. AdaBoost may be used (e.g., best used) to boost the performance of decision trees, base estimator(s), binary classification problems, and/or the like. AdaBoost may be sensitive to noisy data and/or outliers.

ML techniques may be used to perform data reduction, for example, such as stochastic gradient descent (SGD). SGD may include an iterative process used to optimize a function (e.g., objective function). SGD may be used to optimize an objective function, for example, with certain smoothness properties. Stochastic may refer to random probability. SGD may be used to reduce computational burden, for example, in high-dimensional optimization problems. SGD may be used to enable faster iterations, for example, while exchanging for a lower convergence rate. A gradient may refer to the slop of a function, for example, that calculates a variable's degree of change in response to another variable's changes. Gradient descent may refer to a convex function that outputs a partial derivative of a set of its input parameters. For example, a may be a learning rate and Ji may be a training example cost of the ith iteration. The equation may represent the stochastic gradient descent weight update method at the jth iteration. In large-scale ML and sparse ML, SGD may be applied to problems in text classification and/or natural language processing (NLP). SGD may be sensitive to feature scaling (e.g., may need to use a range of hyperparameters, for example, such as a regularization parameter and a number of iterations).

ML techniques may be used to perform data reduction, for example, such as using outlier detection. An outlier may be a data point that contains information (e.g., useful information) on an abnormal behavior of a system described by the data. Outlier detection processes may include univariate processes and multivariate processes.

ML processes may be trained, for example, using one or more training methods. For example, ML processes may be trained using one or more of the following training techniques: supervised learning; unsupervised learning; semi-supervised learning; reinforcement learning, and/or the like.

Figure 8A:
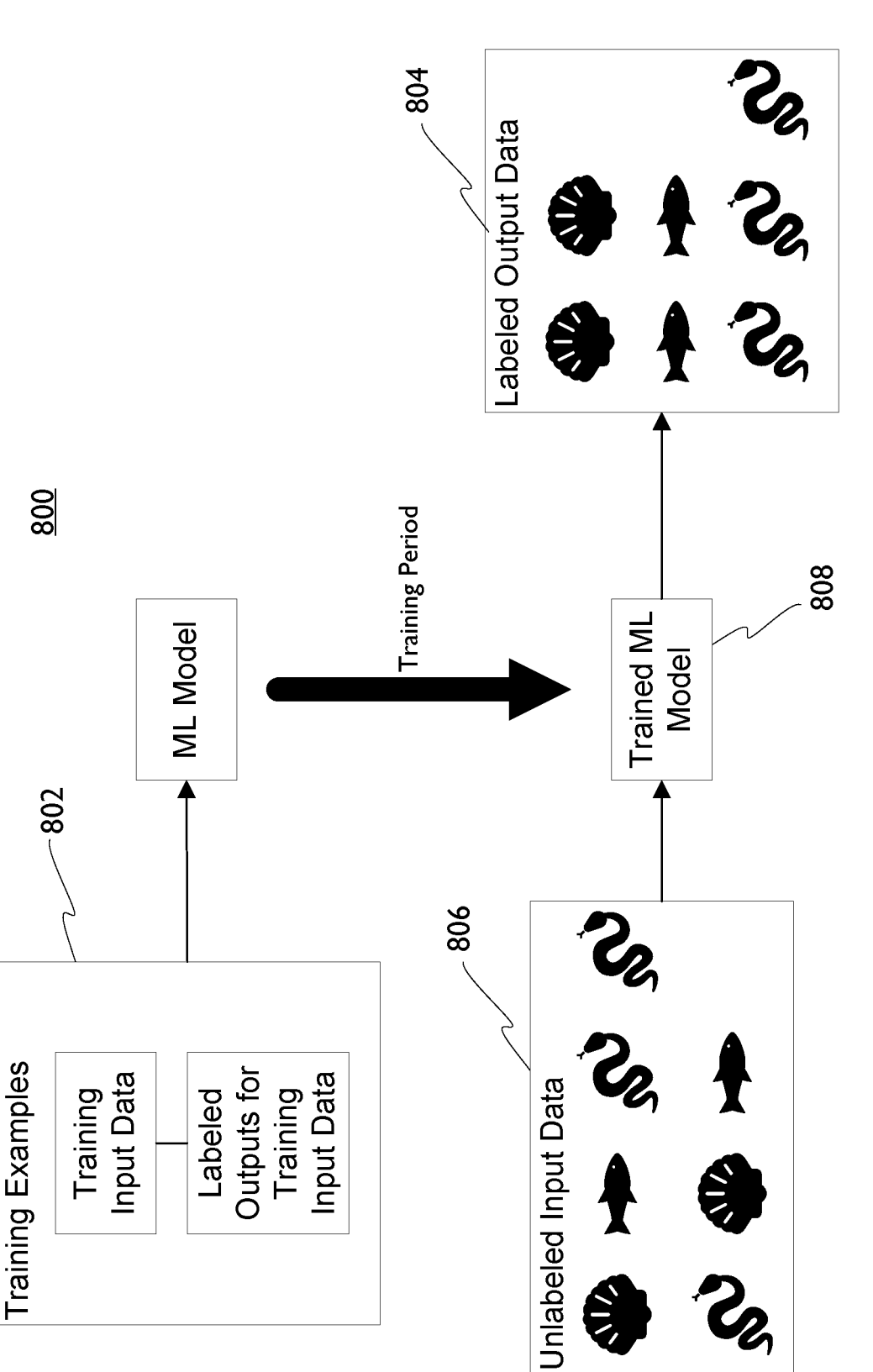
FIGS. 8A&B show an example supervised learning framework and an example unsupervised learning framework, respectively.

Machine learning may be supervised (e.g., supervised learning). A supervised learning algorithm may create a mathematical model from training a dataset (e.g., training data). FIG. 8A illustrates an example supervised learning framework 800. The training data (e.g., training examples 802, for example, as shown in FIG. 8A) may consist of a set of training examples (e.g., input data mapped to labeled outputs, for example, as shown in FIG. 8A). A training example 802 may include one or more inputs and one or more labeled outputs. The labeled output(s) may serve as supervisory feedback. In a mathematical model, a training example 802 may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function (e.g., a trained ML model 808) may determine the output 804 (e.g., labeled outputs) for one or more inputs 806 that may not have been a part of the training data (e.g., input data without mapped labeled outputs, for example, as shown in FIG. 8A). Example algorithms may include linear regression, logistic regression, neutral network, nearest neighbor, Naive Bayes, decision trees, SVM, and/or the like. Example problems solvable by supervised learning algorithms may include classification, regression problems, and the like.

Figure 8B:
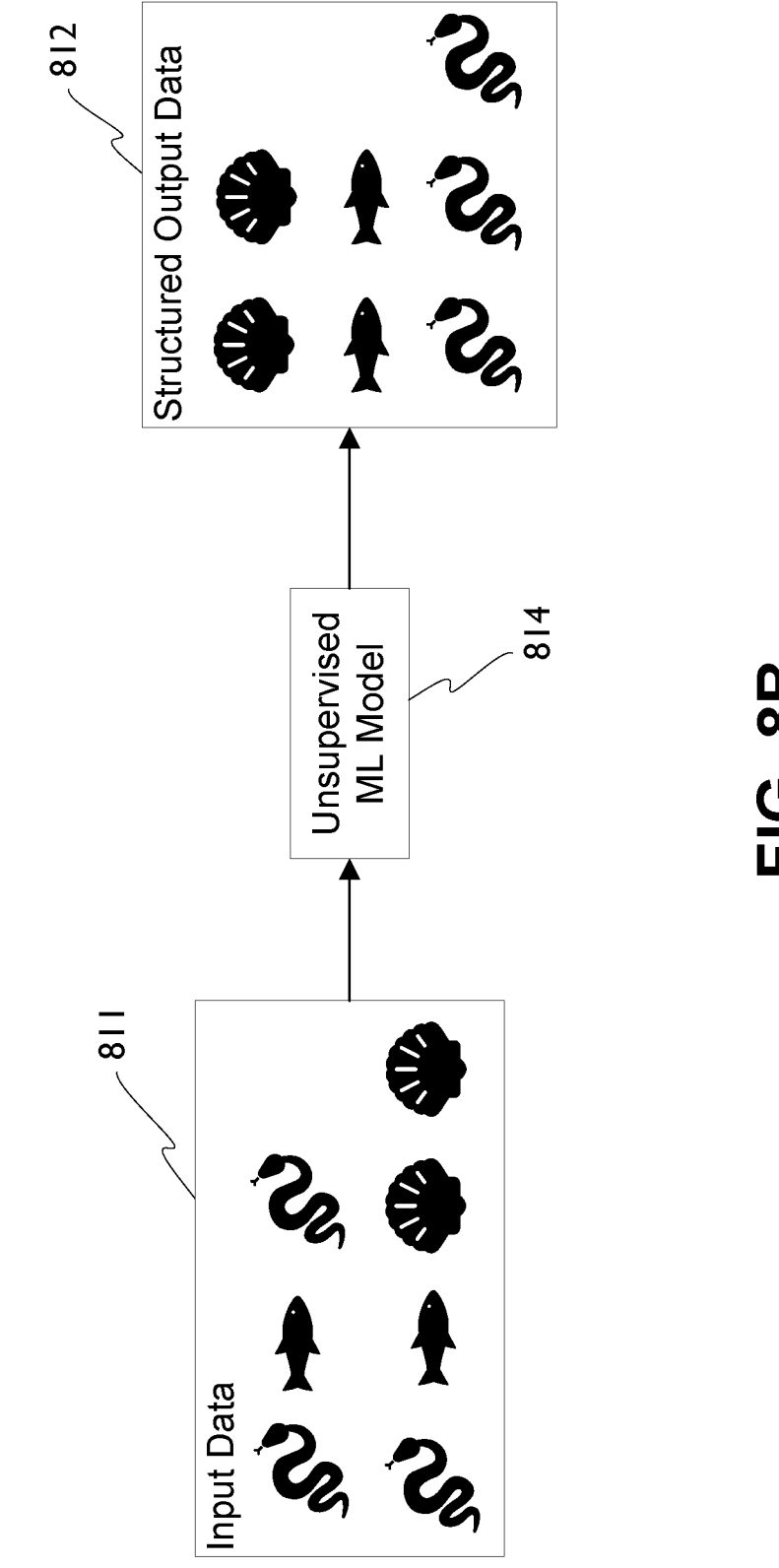

Machine learning may be unsupervised (e.g., unsupervised learning). FIG. 8B illustrates an example unsupervised learning framework 810. An unsupervised learning algorithm 814 may train on a dataset that may contain inputs 811 and may find a structure 812 (e.g., pattern detection and/or descriptive modeling) in the data. The structure 812 in the data may be similar to a grouping or clustering of data points. As such, the algorithm 814 may learn from training data that may not have been labeled. Instead of responding to supervisory feedback, an unsupervised learning algorithm may identify commonalities in training data and may react based on the presence or absence of such commonalities in each training datum. For example, the training may include operating on a training input data to generate an model and/or output with particular energy (e.g., such as a cost function), where such energy may be used to further refine the model (e.g., to define model that minimizes the cost function in view of the training input data). Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like Machine learning may be semi-supervised (e.g., semi-supervised learning). A semi-supervised learning algorithm may be used in scenarios where a cost to label data is high (e.g., because it requires skilled experts to label the data) and there are limited labels for the data. Semi-supervised learning models may exploit an idea that although group memberships of unlabeled data are unknown, the data still carries important information about the group parameters.

Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent. Examples algorithms may include Q-Learning, Temporal Difference (TD), Deep Adversarial Networks, and/or the like.

Reinforcement learning may include an algorithm (e.g., agent) continuously learning from the environment in an iterative manner. In the training process, the agent may learn from experiences of the environment until the agent explores the full range of states (e.g., possible states). Reinforcement learning may be defined by a type of problem. Solutions of reinforcement learning may be classed as reinforcement learning algorithms. In a problem, an agent may decide an action (e.g., the best action) to select based on the agent's current state. If a step if repeated, the problem may be referred to as an MDP.

For example, reinforcement learning may include operational steps. An operation step in reinforcement learning may include the agent observing an input state. An operation step in reinforcement learning may include using a decision making function to make the agent perform an action. An operation step may include (e.g., after an action is performed) the agent receiving a reward and/or reinforcement from the environment. An operation step in reinforcement learning may include storing the state-action pair information about the reward.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronic medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g. logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. Such data record may be converted to a flat file format for model training. Such data may be mapped to numeric values for model training. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0) and 1 for model training. For example, the preprocessed data may include data values that carry more meaning when aggregated.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

ML techniques may be used independently of each other or in combination. Different problems and/or datasets may benefit from using different ML techniques (e.g., combinations of ML techniques). Different training types for models may be better suited for a certain problem and/or dataset. An optimal algorithm (e.g., combination of ML techniques) and/or training type may be determined for a specific usage, problem, and/or dataset. For example, a process may be performed to for one or more of the following: choose a data reduction type, choose a configuration for a model and/or algorithm, determine a location for the data reduction, choose an efficiency of the reduction and/or result, and/or the like.

For example, a ML technique and/or combination of ML techniques may be determined for a particular problem and/or use case. Multiple data reduction and/or data analysis processes may be performed to determine accuracy, efficiency, and/or compatibility associated with a dataset. For example, a first ML technique (e.g., first set of combined ML techniques) may be used on a dataset to perform data reduction and/or data analysis. The first ML technique may produce a first output. Similarly, a second ML technique (e.g., second set of combined ML techniques) may be used on the dataset (e.g., same dataset) to perform data reduction and/or data analysis. The second ML technique may produce a second output. The first output may be compared with the second output to determine which ML technique produced more desirable results (e.g., more efficient results, more accurate results). Multiple ML techniques may be compared with the same dataset to determine the optimal ML technique (s) to use on a future similar dataset and/or problem.

In examples, in a medical context, a surgeon or healthcare professional may give feedback to ML techniques and/or models used on a dataset. The surgeon may input feedback to weighted results of a ML model. The feedback may be used as an input by the model to determine a reduction method for future analyses.

In examples, a data analysis method (e.g., ML techniques to be used in the data analysis method) may be determined based on the dataset itself. For example, the origin of the data may influence the type of data analysis method to be used on the dataset. System resources available may be used to determine the data analysis method to be used on a given dataset. The data magnitude, for example, may be considered in determining a data analysis method. For example, the need for datasets exterior to the local processing level or magnitude of operational responses may be considered (e.g., small device changes may be made with local data, major device operation changes may require global compilation and verification).

Such ML techniques may be applied to surgical information (e.g., a combination of information flows of surgical information in FIGS. 7A-D) to generate useful ML models.

Figure 9:
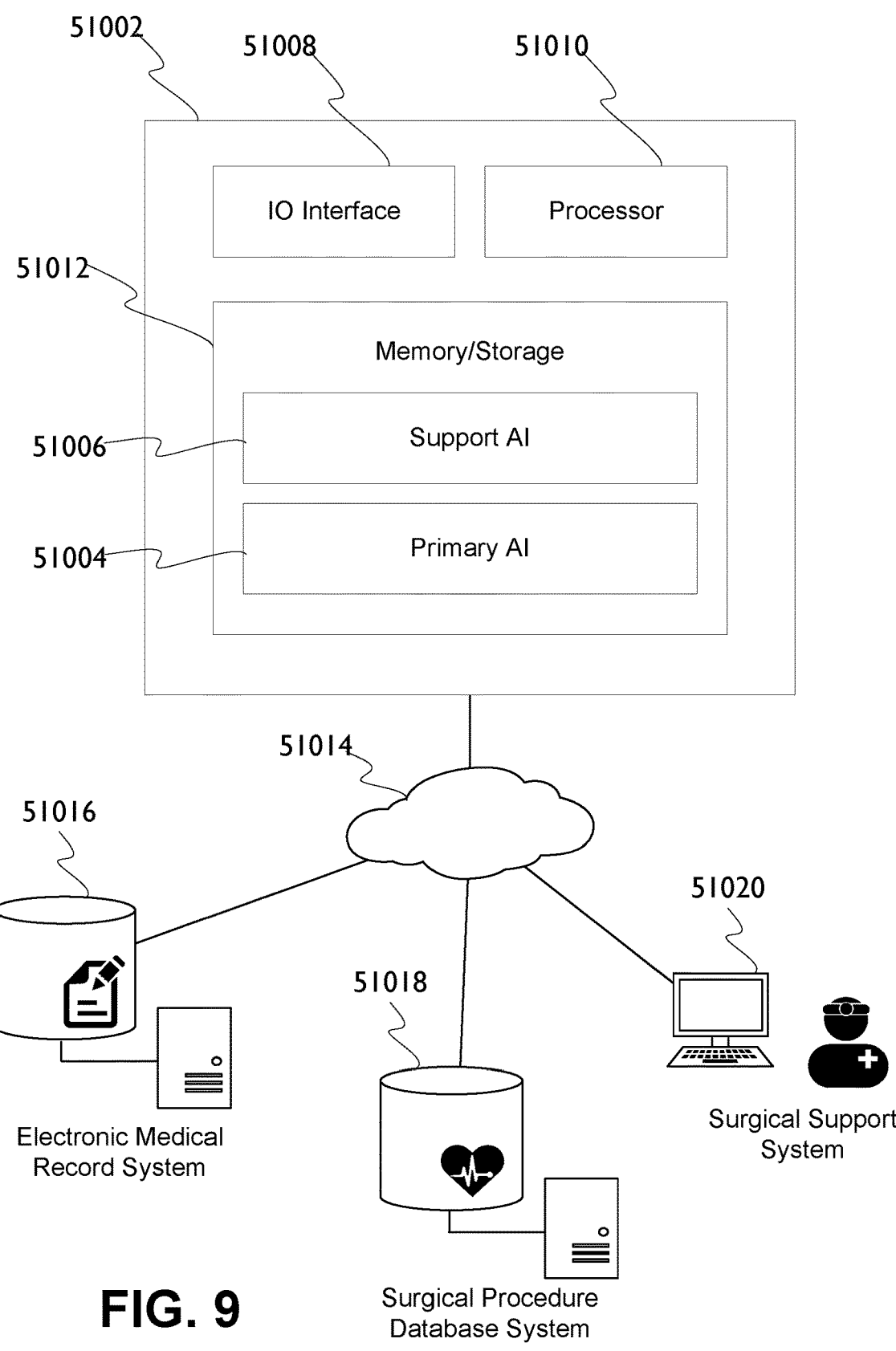
FIG. 9 is a block diagram of an example computing system with example primary and support artificial intelligence (AI) models.

FIG. 9 is a block diagram of an example computing system 51000 with an example primary artificial intelligence (AI) model 51004 (e.g., a primary neural network) and an example support AI model 51006 (e.g., a support neural network). A computing device 51002 may be used to enhance the preparation of a surgical procedure plan. The device 51002 may include an IO interface 51008, a processor 51010, memory/storage 51012, and the like.

The IO interface 51008 may include any hardware, software, or combination thereof, suitable for providing input and/or output of data or information. The IO interface 51008 may include a human interface device such as a display, keyboard, mouse, and the like. The IO interface 51008 may include a computer network input/output interface, such as an ethernet interface, for example.

The processor 51010 may include any hardware, software, or combination thereof suitable for processing data. The processor 51010 may operate according to a set of computer instructions to perform computer tasks. For example, the processor 51010 may include an Intel based general purpose processor, for example. The processor 51010 may operate in accordance with instructions and/or data stored in the memory/storage, for example. The processor 51010 may include an AI accelerator, such as an application-specific integrated circuit or other hardware specialized for AI processing. For example, the processor 51010 may include a Tensor Processing Unit (TPU).

The memory/storage 51012 may include any software, hardware, or combination thereof suitable for retaining information. The memory/storage 51012 may include volatile memory, non-volatile memory, and the like. For example, the memory/storage may include random access memory, and/or solid-state drive memory, or the like. The memory/storage memory/storage 51012 may have stored therein instructions and data suitable for implementing one or more artificial intelligence algorithms. For example, the memory/storage 51012 may include and/or retain a primary AI model 51004 and a support AI model 51006.

The primary AI model 51004 and support AI model 51006 may include AI models with the functionality disclosed herein. For example, the primary AI model 51004 and support AI model 51006 may work cooperatively to provide improved surgical support recommendations. The primary AI model 51004 and support AI model 51006 may have any AI architecture and training suitable for recommending surgical procedure information based on training of earlier patient-focused and procedure-focused training data, for example. For example, the primary AI model 51004 and support AI model 51006 may operate based on surgical information, such as the surgical information disclosed with reference, for example, to FIGS. 7A-D herein. For example, the primary AI model 51004 and support AI model 51006 may operate based on surgical information, such as surgical information obtainable via an electronic medical records (EMR) system 51016, a surgical procedure database system 51018, or the like for example.

The device 51002 may interact with a network 51014. For example, the device 51002 may interact with the network 51014 via the IO interface 51008. The network 51014 may provide connectivity between the device 51002 and/or one or more other computing devices, such as the EMR system 51016, the surgical procedure database system 51018, a surgical support system 51020, and the like.

The EMR system 51016 may include any computing system suitable for receiving, managing, retaining, and/or editing electronic medical records. The EMR system 51016 may include features for storing, retrieving, and using patient data. For example, the EMR system 51016 may include features for storing, retrieving, and using patient data in a manner that complies with patient privacy regulations and/or policies. For example, the EMR system 51016 may include the features disclosed in U.S. patent application Ser. No. 17/958,230, titled METHOD FOR HEALTH DATA AND CONSENT MANAGEMENT, filed Sep. 30, 2022, the contents of which are hereby incorporated by reference herein.

For example, EMR system 51016 may include patient data. Patient data may patient-identifying information, healthcare data, and the like. Example patient-identifying information may include, but not limited to, names or part of names, information that may indicate unique identifying characteristic, geographical identifiers, dates directly related to a person, phone number details, fax number details, details of email addresses, social security details, medical record numbers, health insurance beneficiary numbers, account details, certificate or license numbers, vehicle license plate details, device identifiers and serial numbers, website URLs, IP address details, fingerprints, retinal and voice prints, complete face or any comparable photographic images, and/or the like.

The patient data may include general and administrative information, such as patient management information, provider administrative information relating to the patient, billing data, patient demographics, and the like.

Healthcare data may include personal data relating to the physical or mental health of an individual, including the provision of health care services, which reveals information about their health status. Health data may include data collected when a patient has an interaction with a health care provider (e.g., a primary physician, hospital or an organization, such as a universal health service. The health data may include information related to the patient's medical care, including for example, progress notes, vital signs, medical histories, diagnoses, medications, immunizations, allergies, imaging (e.g., radiology images), laboratory and test results, past medical procedures (e.g., past surgical procedures), planned medical procedures (e.g., planned surgical procedures), and the like. The health data may include pre- and post-operative scan data and/or peri-operative imaging data. Such can data and imaging data may be classified and aggregated for analysis and inclusion in an training data set.

The surgical procedure database system 51018 may include any computing systems suitable for maintaining information related to surgical procedures. For example, the surgical procedure database system 51018 may include one or more surgical procedure plans. Surgical procedure plan may include a data structure that incorporates one or more surgical tasks. The surgical procedure database system 51018 may incorporate information related to the performance of various surgical procedures. For example, the surgical procedure database system 51018 may indicate the instruments, surgical setup, specific procedures, anatomical landmarks, and supporting and clinical staff support related information for a particular procedure.

In an example, a surgical procedure plan may include information that outlines the staff, equipment, technique, and steps that may be used to perform a surgical procedure. For example, the procedure plan may include a staff manifest indicating what roles and/or what specific health care professionals are to be involved in the procedure. The procedure plan may include a listing of equipment, such as durable surgical equipment, imaging equipment, instruments, consumables, etc. that may be used during the procedure. For example, the procedure plan may include a pick list for a surgical technician to use to assemble the appropriate tools and materials for the surgeon and the surgery when prepping the operating theater. The procedure plan may include information about the procedure's expected technique. For example, the procedure plans for the same surgical goal may include different methods of access, mobilization, inspection, tissue joining, wound closure, and the like.

The procedure plan may reflect a surgeon's professional judgement with regard to an individual case. The procedure plan may reflect a surgeon's preference for and/or experience with a particular technique. The procedure plan may map specific surgical tasks to roles and equipment. The procedure plan may provide an expected timeline for the procedure.

The procedure plan may include one or more decision points and/or branches. Such decision points and/or branches may provide surgical alternatives that are available for particular aspects of the procedure, where selection of one of the alternatives may be based on information from the surgery itself. For example, the choice of one or more alternatives may be selected based on the particular planes of the particular patient's anatomy, and the surgeon may select an alternative based on her assessment of the patient's tissue during the live surgery.

The procedural plan may include one or more contingencies. These may include information about unlikely but possible situations that may arise during the live surgery. The contingencies may include one or more surgical tasks that may be employed if the situation does occur. The contingencies may be used to ensure that adequate equipment, staff, and/or consumables are at the ready during the procedure.

The procedure plan may be recorded in one or more data structures. A procedure plan data structure may be used to record data about a future live surgery, about a completed live surgery, about a future simulated surgery, about a completed simulated surgery, and the like. A procedure plan data structure for live surgeries may be used by the computer-implemented interactive surgical system, such as the surgical computing system 704 disclosed herein. For example, the procedure plan data structure for live surgeries may be used by surgical computing system 704 to enhance situational awareness and/or the operational aspects of a computer-implemented interactive surgical system 730. The procedure plan data structure for live surgeries may be used by the surgical computing system 704 to record discrete elements of the live surgery for structured analysis.

The procedure plan may be stored in any data structure suitable for storing, adding, removing, editing, and processing structured information. For example, the procedure plan may be stored in a data structure disclosed in U.S. patent application Ser. No. 17/332,594, titled METHODS FOR SURGICAL SIMULATION, filed May 27, 2021, the contents of which are hereby incorporated by reference herein. For example, the procedure plan may be stored in a relational database, such as one or more tables of a relational database for example.

The surgical support terminal 51020 may include a user interface terminal suitable for presenting and receiving information. For example, the surgical support terminal 51020 may provide an interface for a surgeon to prepare for a particular surgery. For example, the surgical support terminal 51020 may query the electronic medical record system 51016 for information regarding a patient who will undergo a particular procedure. The surgical support system 51020 may query the surgical procedure database system 51018 for information related to the surgical procedure to be performed on that patient.

The surgical support system 51020 may enable the surgeon to refine, edit, modify, adjust the surgical procedure plan. For example, the surgeon may add surgical tasks, remove surgical tasks, modify surgical tasks, and the like. The surgical support system 51020 may enable the surgeon to modify the surgical procedure plan by incorporating particular surgical instruments, by modifying the staff required, by revising surgical steps, by adjusting one or more parameters associated with the surgical steps, and the like. The surgical support system 51020 may provide the surgeon with various medical imaging related to the procedure. For example, the surgical support system 51020 may provide a 2D and/or 3D image to the surgeon for preparing for a surgical procedure.

The surgical support system 51020 may interact with the device 51002 to further modify and/or enhance the surgical procedure plan. For example, the device 51002 may provide a primary AI model 51004 and a support AI model 51006 to generate an output indicative of a recommended, modified procedure plan based on an initial proposed procedure plan. The recommended, modified procedure plan may be outputted at the surgical support system 51020, for example. The recommended, modified procedure plan may be outputted at the surgical support system 51020, for example, for further review, analysis, revision, and the like.

Figure 10:
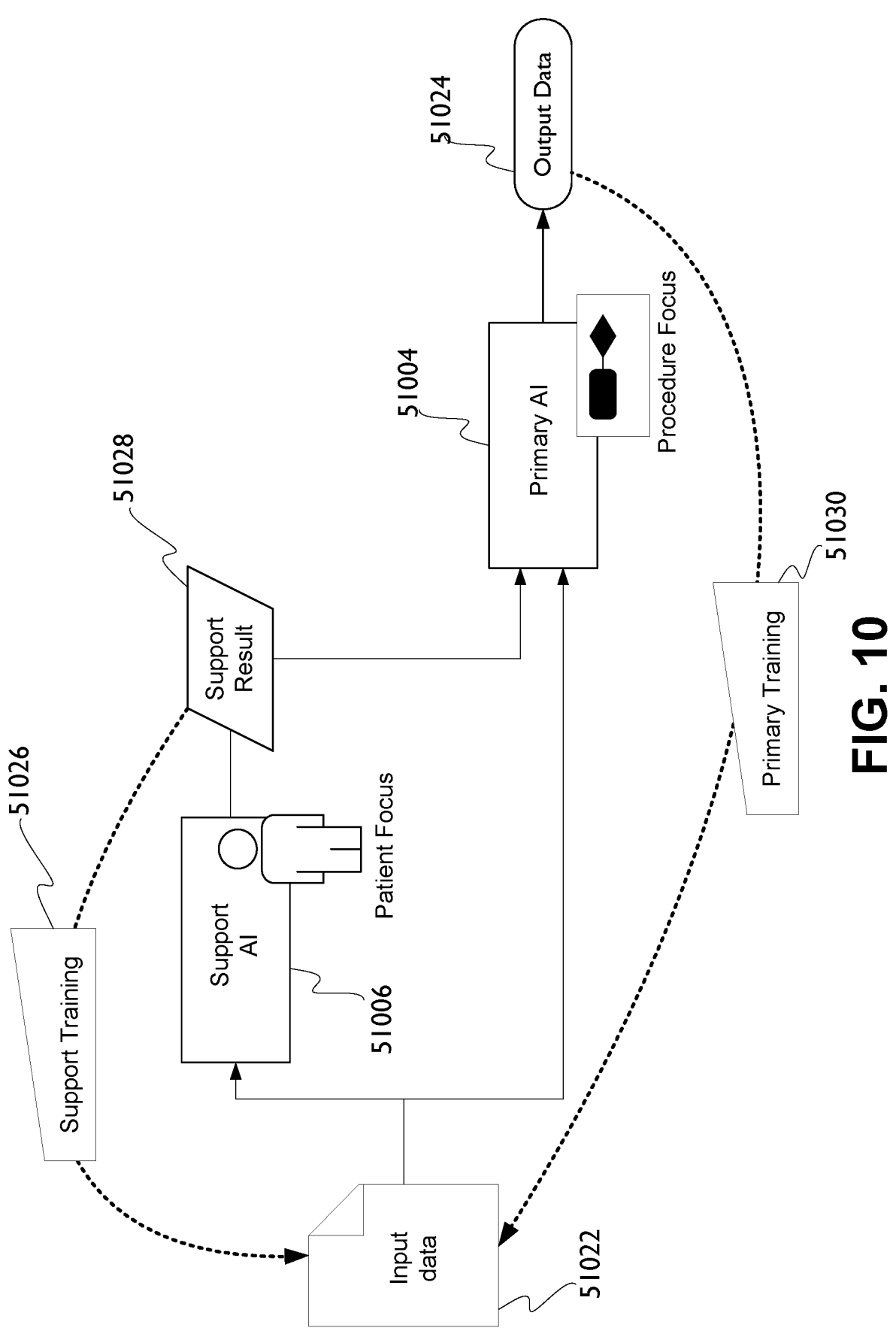
FIG. 10 is an architecture diagram illustrating the use and training of example primary and support AI models.

FIG. 10 is an architecture diagram illustrating the use and training of example primary AI model 15004 and a support AI model 51006 for modifying a procedure plan. Here, input data 51022 may be provided to a primary AI model 51004 and a support AI model 51006. The primary AI model 51004 may be implemented as a primary neural network. The support AI model 51006 may be implemented as a secondary neural network. The input data may include information suitable for the primary AI model 51004 and support AI model 51006 to generate a recommendation. For example, the input data may include information indicative of a surgical patient. For example, the input data may include information indicative of a target procedure. For example, the input data may include information indicative of a surgical patient a proposed procedure plan. For example, the input data may include information indicative of a surgical patient, and target procedure, and a proposed procedure plan. The input data may be received from the surgical support system 51020, for example.

In an example, the input data 51022 may include basic patient demographic information, information indicative of the patient's tissue condition, patient imaging, prescription information, a procedure identifier, a data structure defining the proposed procedure plan (including, for example, procedure steps, instruments, and parameters related to instrument settings and use), and the like.

The support AI model 51006 may include a model trained according to support training data 51026 with a patient focus. For example, the support AI model 51006 may a include a neural network, such as recommendation engine. The support AI model 51006 may be trained to provide an intermediate output, such as a support result 51028. The support result may represent a refined aspect of the patient data presented at the input data 51022. In effect, for example, the support training data 51026 may provide "gap filling" for the input patient data based on the model's representation of similarly situated patients in the training data 51026.

In an example, the support AI model 51006 may be trained to isolate anatomical elements. The support AI 51006 may generate one or more support results 51028. For example, the support results 51028 may include an isolated version of the patient-specific anatomy. In this example, the isolated version of the patient-specific anatomy may include one or more data elements indicative of the patient anatomy targeted by the target procedure. For example, the support AI 51006 may include elements of architecture and training like that disclosed in Domingues, I., Pereira, G., Martins, P. et al. Using deep learning techniques in medical imaging: a systematic review of applications on CT and PET. Artif Intell Rev 53, 4093-4160 (2020), the contents of which are hereby incorporated by reference.

In an example, the support AI model 51006 may be trained to provide anatomical landmarks relevant to the patient anatomy. For example, the support results 51028 may include registration information. For example, the registration information may be one or more anatomical landmarks. Here, the support AI may be trained using support training data 51026 that is independent of the target procedure (i.e., support training data need not be taken from surgical information associate with procedures that match the target procedure). For example, the support AI 51006 may include elements of architecture and training like that disclosed in Unberath M, Gao C, Hu Y, Judish M, Taylor RH, Armand M and Grupp R., The Impact of Machine Learning on 2D/3D Registration for Image Guided Interventions: A Systematic Review and Perspective. Front. Robot. AI 8:716007 (2021), the contents of which are hereby incorporated by reference.

The input data 51022 and the support results 51028 may be provided to the primary AI model 51004. The primary AI model 51004 may process the support result and some or all of the input data. The support results 51028 may be modified by expert intervention. For example, the support results 51028 may be presented separately to a surgeon at a surgical support system 51020, for example. The support result 51028 may be input to the primary AI model 51004 to further enhance the prediction/recommendation with regard to providing a modified procedure plan.

The primary AI model 51004 may be trained with primary training data 51030 based on data associated with procedure plans and corresponding patient outcomes. For example, the support AI model 51006 and the primary AI model 51004 may be trained independently. The training data 51030 may include data with a procedure focus. For example, the training data 51030 may include information regarding procedure plans and corresponding patient outcomes with patients that are similar and dissimilar to the patient represented by the patient information int the input data 51022. For example, the primary AI model 51004 may employ one or more elements of architecture and training like that disclosed in U.S. Patent Application Publication US2019/0073632A1, titled PROVIDING IMPLANTS FOR SURGICAL PROCEDURES, filed Oct. 30, 2018, the contents of which are hereby incorporated by reference.

The primary AI model 51004 may generate output data 51024 which may represent one or more recommendations and/or modifications to the proposed procedure plan provided in the input data 51022. For example, the primary AI model 51030 may output a modified procedure plan that is different from the proposed procedure plan. The differences may include differences in surgical steps, instrumentation, instrumentation use and/or settings, anatomical references (such as dissection paths and/or port placement for example), and the like. In an example, the modified procedure plan may identify a surgical instrument. The modified procedure plan may identify a surgical instrument that is different than that identified by the proposed procedure plan. In an example, the modified procedure plan may identify tumor margins. For example, the tumor margins may be different than that identified by the proposed procedure plan. In an example, the modified procedure plan may identify a mobilization approach. This mobilization approach may be different than that identified by the proposed procedure plan.

Such modifications to the procedure plan may be a product of the input data 51022 and the support result 51028. For example, the support result 51028 may include a patient specific mapping, such as a patient specific anatomy associated with a target procedure. And the primary AI model 51004 may leverage the patient specific anatomy to modify aspects of the procedure plan for the particular patient. The primary AI model 51004 may recommend a procedure plan in view of the support results 51028 which is different than had the support results 51028 not been used.

As illustrated here, in FIG. 10, the support AI model 51006 is trained in view of patient focused training data 51026 and the primary AI model 51004 is trained in view of procedure focused training data 51030, such that the support results 51028 represent patient focused input to the primary AI model. In an example, the support AI model may be designed and trained in view of procedure focused training data and the primary AI model may be designed and trained in view of patient focused training data, such that the support results, in this example, may represent procedure focused input to the primary AI model.

Figure 11:
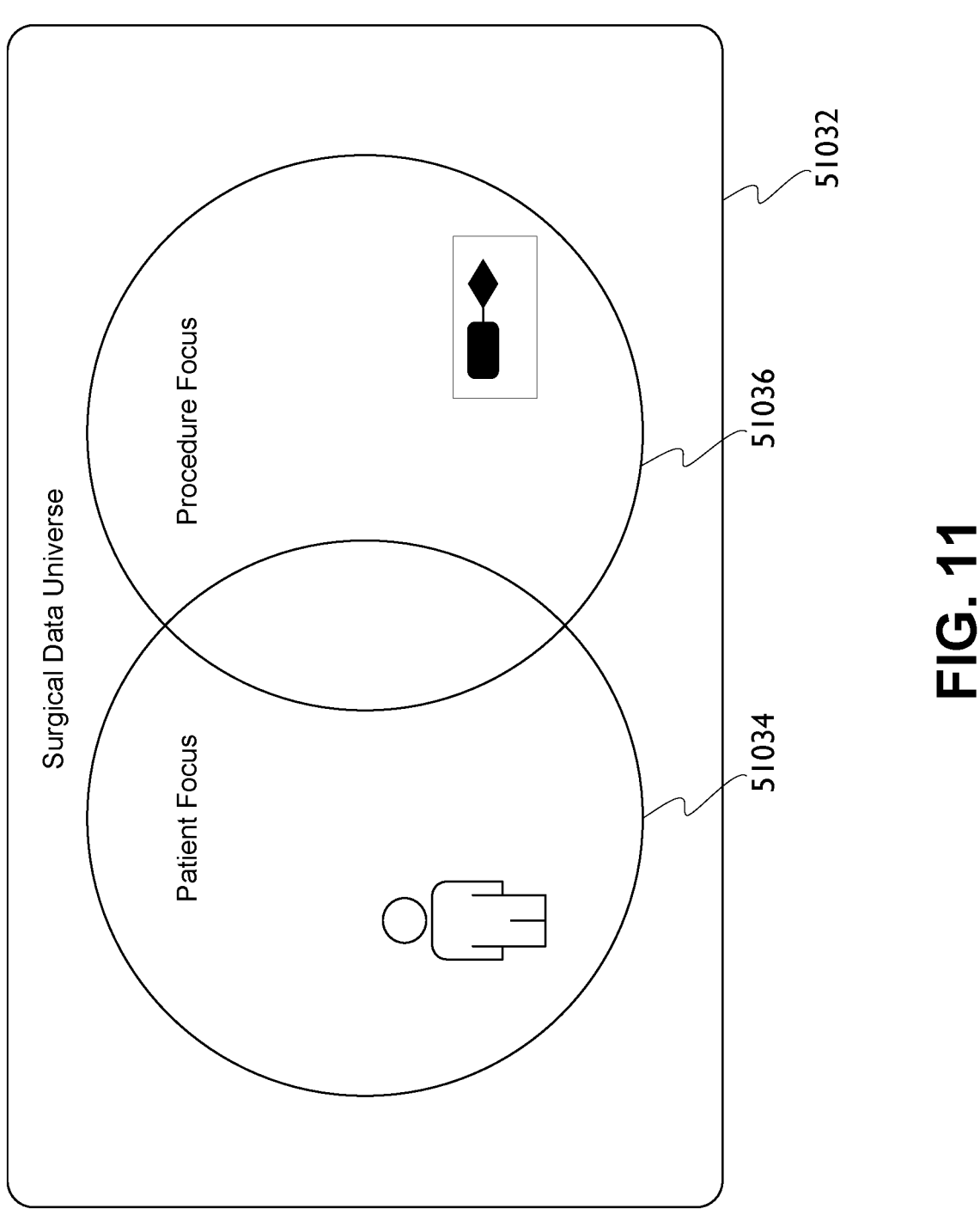
FIG. 11 illustrates a logic view of the universe of surgical data.

FIG. 11 illustrates a logic view of the universe of surgical data 51032. The AI approach disclosed herein, advantageously uses differently focused data sets for each module to provide a modified procedure plan that takes advantage of the distinct learning available from the differently focused data sets. For example, one model may be trained in view of data selected from a patient focused subset 51034 of universe of available surgical data 51032, and another model may be trained in view of data selected from a procedure focused subset 51036 of the universe of available surgical data 51032. In an example, and as illustrated in FIG. 11, the patient focused subset 51034 and the procedure focused subset 51036 may be partially overlapping subsets. In an example, the patient focused subset 51034 and the procedure focused subset 51036 may be fully distinct from each other.

In an example, multiple versions of the support AI model and the primary AI model may be used, with an analysis of their respective outputs to identify a preferred combination. By leveraging at least two versions of models on a same or similar dataset may be used to determine relationships each could identify from surgical and/or interventional data. The results may be then used to produce a hybrid composite algorithm. Such an approach may be used to defining which module is positioned in which role (e.g., support or primary). In an example, such a hybridization may generate different composite algorithm steps for use for each distinct data set.

In an example, multiple versions of the support AI model and the primary AI model may be used, with an analysis of their respective outputs to group models that achieved similar results. And other models may be highlighted based on outputs that that result in divergent results. Here, such divergent outputs may identify outliers that are relevant (e.g., not merely noise). Such models may be incorporated as support AI models, as disclosed herein, to enable the overall system to take advantage of such relevant outliers.

To illustrate, Korean-based surgical data may represent an improved outcome regarding colon cancer due to diet, such a data set may drive results in outlier output data. Japanese-based surgical data, by contrast, may present a similar outlier effect for gastric cancer, but here not because of diet, but because of the meticulousness of dissection and additional surgical efforts to prevent mobilization of cancer cells. Such an outlier may be difficult to identify appropriate by traditional means. Here, for example, the beneficial learning available in the Japanese-based data set may be overshadowed by a regional confounding factor (e.g., H-pyloi bacteria may increase ulceration because of inadequate water supply treatments, which degrade the surgical outcomes in the gastric cancer data). The architecture disclosed herein may enable the identification and use of beneficial data sets apart from mere regional differences.

In another example, data extracted, such as the support results disclosed herein, may be used to determine a vector directionality of improved performance. For example, localized and/or patient specific data may be approximate and/or may correlate a directional result (e.g., indicating better or worse results) based on the specifics of the patient (e.g., physiology, anatomy, disease state, etc.) and the constraints of the surgery itself (e.g., surgical approach, disease intensity, secondary comorbidities, complications, etc.). Here, a base case may be used based on global and/or regional outcomes. And the base case may be adjusted with the patient specific extracted data to provide an improved result. For example, the primary AI may be trained according to such global and/or region outcomes and the support AI may be trained according to such patient specific information.

Such an approach may enable the surgeon to allow for a directionality and magnitude impact based on these input aspects.

Figure 12:
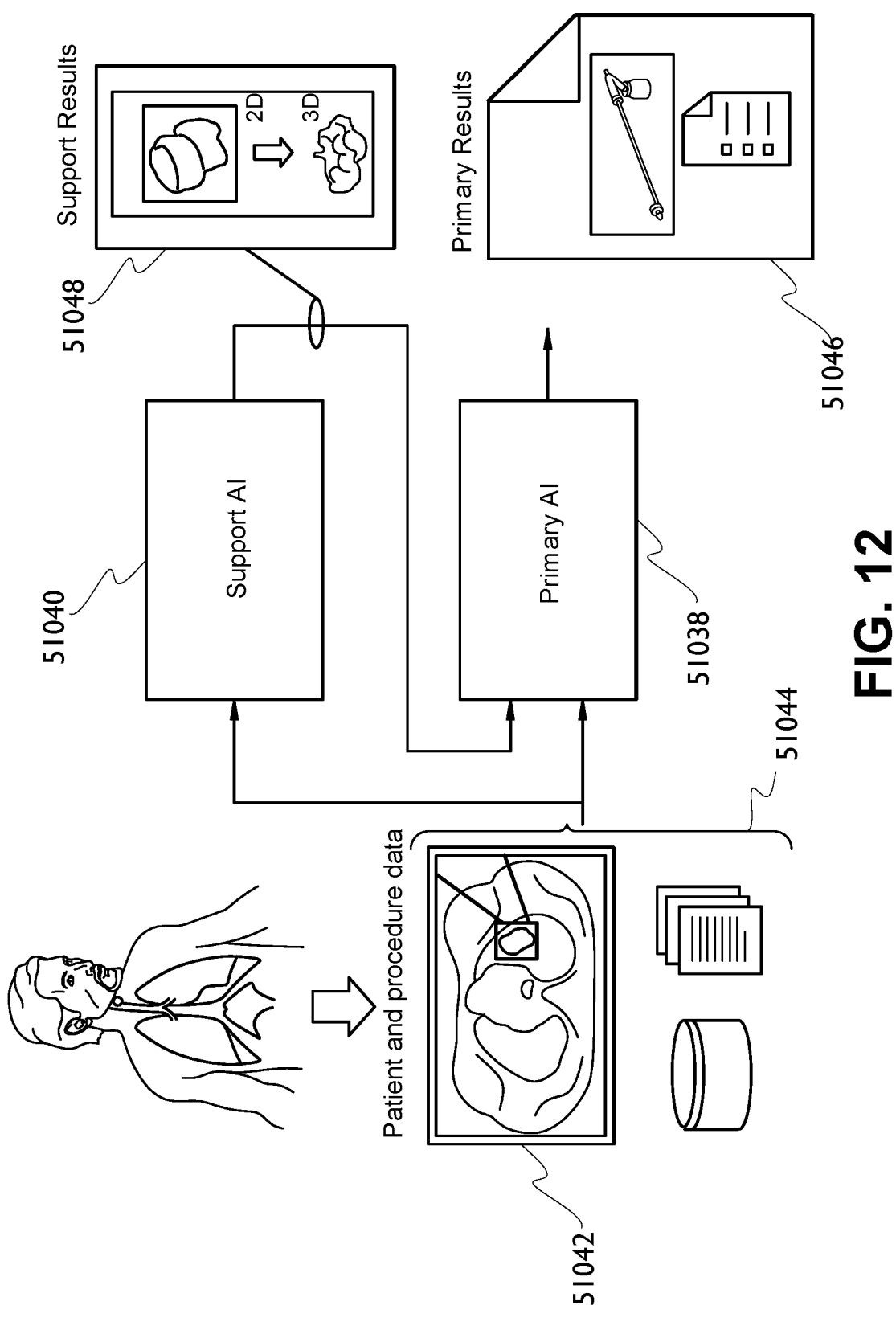
FIG. 12 illustrates the use of example primary and support artificial intelligence AI models in thoracic surgery planning.

FIG. 12 illustrates the use of example primary 51038 and support 51040 AI models in thoracic surgery planning. Here, a patient may undergo additional imaging 51042, consistent with views used in the support AI training data. The support AI 51040 may provide support results 51048 that better identify the relevant anatomy.

In an example, the support AI may include training data including 2D and 3D (e.g., taken via laparoscopic imaging systems with structured light. See: Locally displayed coordinate system is further described in U.S. patent application Ser. No. 16/729,747, titled DYNAMIC SURGICAL VISU-ALIZATION SYSTEMS, filed Dec. 31, 2019, which is incorporated by reference herein in its entirety) pairs.

In an example, such additional imaging 51042, taken over time, in combination with the support AI 51040 may generate support results that better evaluate the volume of a tumor over time. The support AI 51040 may leverage landmarks within the images and the training data to assess volume, which may be available in the support results 51048. Further, this approach (and/or an automated segmentation of scan data) may ultimately be used to evaluate the effectiveness of non-surgical therapies, e.g., pharmaceutical therapies. The primary AI training set, in turn, may be expanded to incorporate such non-surgical therapies generally.

The primary/support approach may be used to leverage alternative treatment options, incorporated into the primary AI training data, to determine if there is a more optimal treatment. The primary AI output data 51046 may highlight modifications to the procedure plan impacts issues such as complication rates, specialized tools, or the like.

Figure 13:
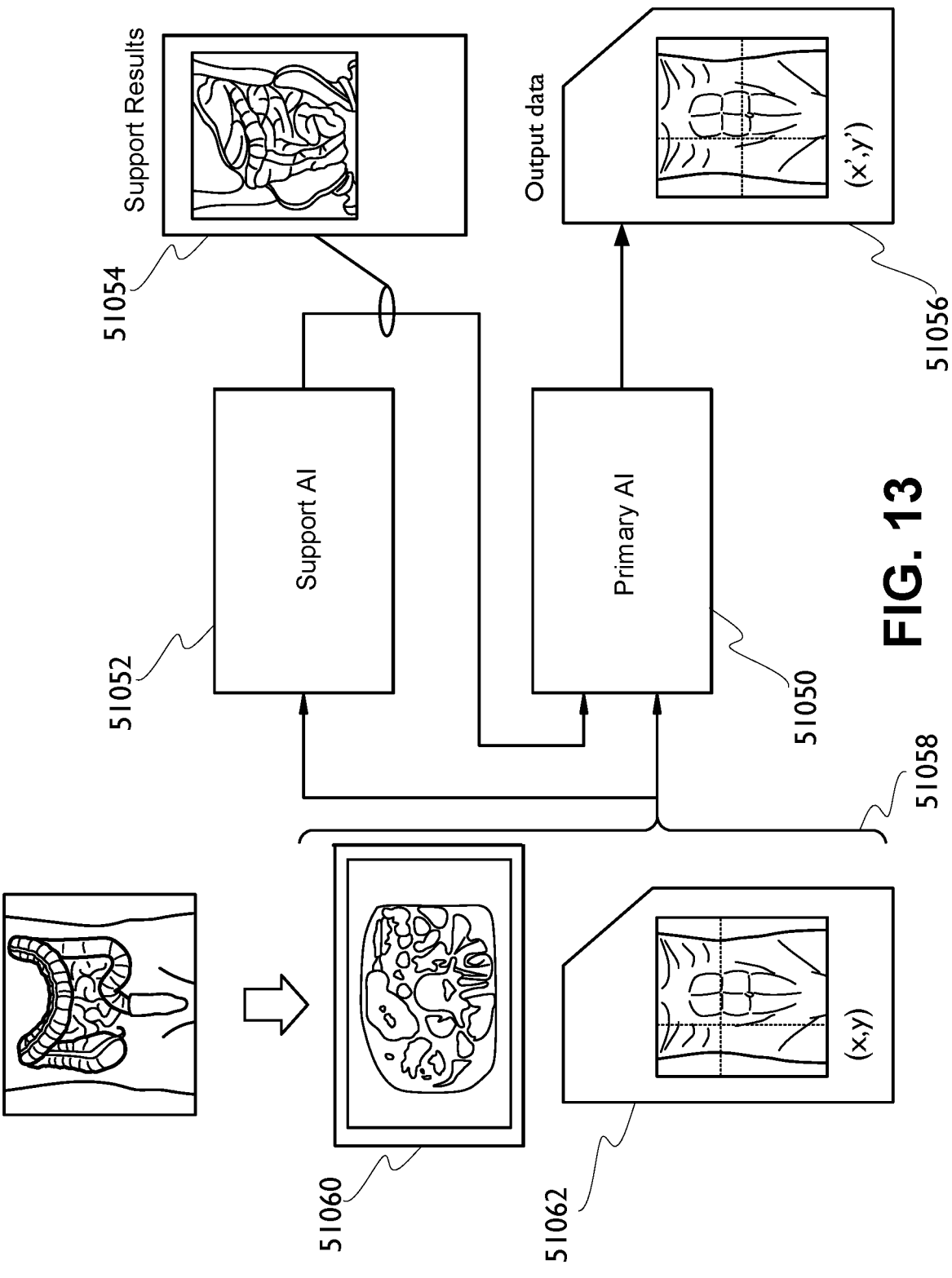
FIG. 13 illustrates use of example primary and support artificial intelligence AI models in abdominal surgery planning.

FIG. 13 illustrates use of example primary 51050 and support 51052 artificial intelligence AI models in abdominal surgery planning. Here, the support AI 51052 may be used to extract geometry data as support results 51054 that may be leveraged in the selection of procedure step parameters, such as the selection of instrumentation, implant sizing, configuration, usage location (primary results 51056, illustrated in FIG. 13)

For example, the input data 51058 may include preoperative imaging 51060 and a proposed procedure plan 51062 with procedure step parameters such as coordinates indicating a usage location. The support results 51054 may provide a more robust and granular understanding of the patient's relevant anatomy. And the primary AI 51050 may be trained with procedural data that includes coordinates. Accordingly, the output data 51056 may include a resultant modification to the procedure plan that includes a second set of coordinates that is different from those provided in the proposed procedure plan 51062.

For example, the overall operational cavity and/or gross parameters may be used to determine the diameter size of a device modification. For example, the patient's anatomical geometry (e.g., colon size) may be enhanced by the support AI 51052 and may facilitate the primary AI 51050 to recommend a more appropriate procedure step parameter (e.g., a modified sized diameter of the head of the circular stapler for the anastomotic reconnection step). In another example, enhanced determination of bone size, defect size, and/or orientation by the support AI 51052 may facilitate definition of an orthopaedic implant by the primary AI 51050. In another example, enhanced determination of the size of the esophageal sphincter region of the unsupported opening (resting size) of the sphincter by the support AI

51052 may facilitate selection of a Torax LINX device size and/or collapsing force by the primary AI 51050.

In another example, enhanced determination of the size of a tumor by the support AI 51052 may facilitate selection of a Torax LINX device size and/or collapsing force by the primary AI 51050.

In another example, enhanced determination of the size of the esophageal sphincter region of the unsupported opening (resting size) of the sphincter by the support AI 51052 may facilitate selection extraction pouch size and/or insertion location/orientation by the primary AI 51050.

In another example, enhanced determination anatomical geometry by the support AI 51052 may facilitate selection of the correct sizing/version of implants and/or selection of instruments and/or access ports by the primary AI 51050.

In another example, enhanced determination anatomical geometry by the support AI 51052 may facilitate the automatic registration and adaptation of related imaging means or images to coalesce them into a single overlaid image. Here, the support AI 51052 may identify salient geometry, extractions of which may be used to identify perspective, scaling, distortion, foal length, and the like. In turn, the primary AI 51050 may be trained to apply filters to the imaging, preparing it for cooperative use with other imaging with common salient geometry In another example, enhanced determination anatomical geometry by the support AI 51052 may facilitate identification of anatomical landmarks by the primary AI 51050 for aspects of the modified procedure plan in the output data 51056, such as orientation, direction instructions, identification of tissue and/or organ planes, and the like. Such modifications being exceptionally useful to the surgeon for navigation of dissection during the surgery.

Figure 14:
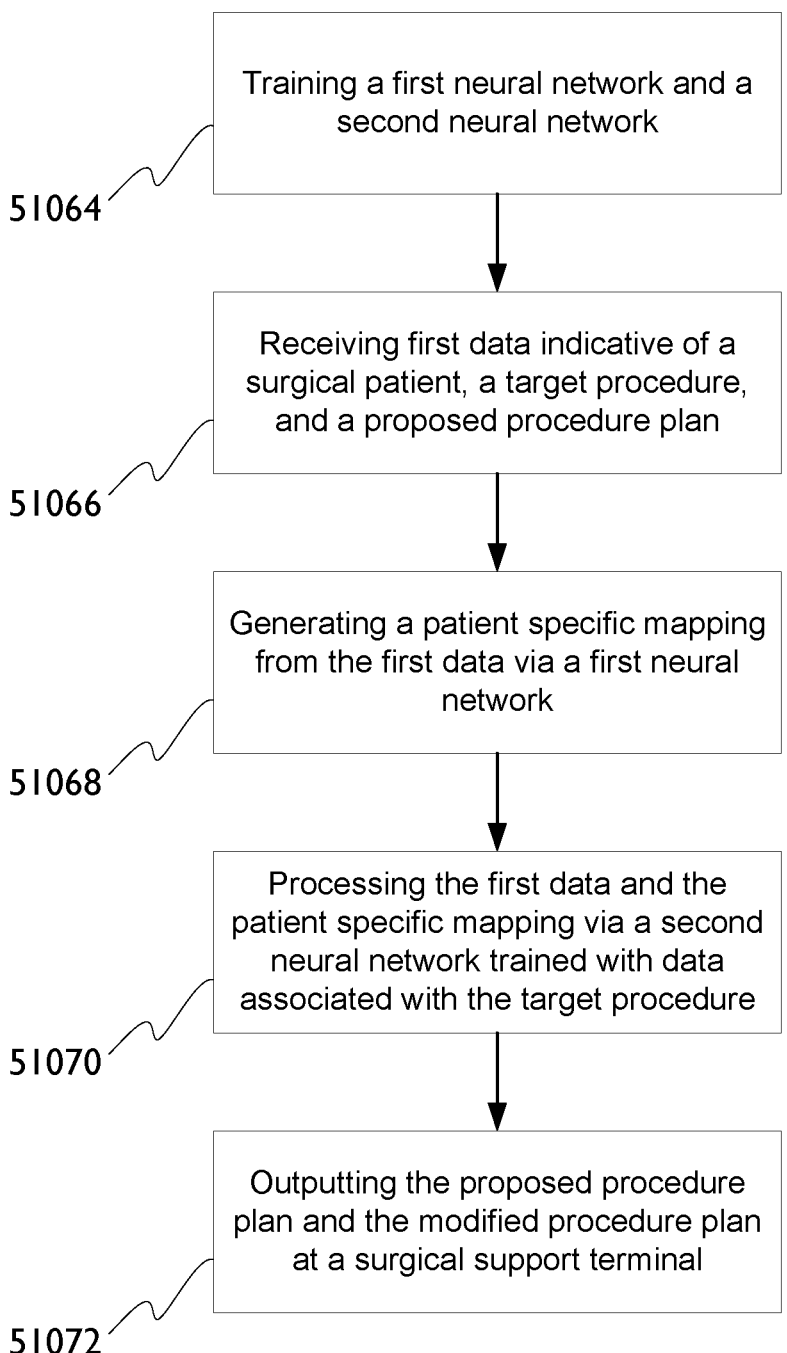
FIG. 14 is a flow diagram of an example process employing primary and support artificial intelligence AI models in surgical planning.

FIG. 14 is a flow diagram of an example process employing primary and support artificial intelligence AI models in surgical planning. At 51064, a first neural network and a second neural network may be trained. For example, the first neural network and a second neural network may be trained independently of each other. For example, the first neural network may be trained to isolate anatomical elements. For example, the first neural network may be trained to generate relative anatomical positioning.

The second neural network may be trained to recommend procedure plans associated with improved patient outcomes. For example, the second neural network may be trained with procedure plans from previously performed procedures and their corresponding patient outcomes. The second neural network may also be trained according to anatomical mapping associated with those previously performed procedures. The second neural network may be trained with data associated with a target procedure. For example, the second neural network may be associated with a particular general class of procedures.

The first neural network may be trained with patient focus (e.g., training data may be used from surgical data with relevant patient attributes regardless of the particular procedures associated with the source training data). The second neural network may be trained with a procedure focus (e.g., training data may be used from surgical data with a common procedure type regardless of the particular patients associated with the source training data). In an example, in the context of lung surgery or a lung resection surgery, the second neural network may be trained with procedure plans, patient specific mappings, and patient outcomes of other lung resection surgeries, and the first neural network may be trained with patient imaging and corresponding anatomical isolated information, regardless of the procedure being performed. Here, the patient specific mapping associated with the first neural network may be used as a data element by the second neural network.

At 51066, the first data may be received. The first data may be indicative of a surgical patient, a target procedure, and a proposed procedure plan, for example. Here, the target procedure may be used to associate the first data with a particular second neural network. The surgical patient aspect of the first data may include patient bibliographic data and/or patient imaging data. The procedure plan may include one or more data elements that indicate and characterize a particular instance of the target procedure.

At 51068, a patient specific mapping may be generated. For example, the patient specific mapping may represent support results generated from the first neural network to support operation of the second neural network. The patient specific mapping may be generated from the first data. The patient specific mapping may be generated from the first data via the first neural network.

At 51070, the first data and the patient specific mapping may be processed. The first data and the patient specific mapping may be processed via the second neural network. The first data and the patient specific mapping may be processed via the second network in accordance with the techniques disclosed herein. And at 51072, a modified procedure plan may be outputted. For example, the modified procedure plan may be outputted at a surgical support system. In an example, the output of the surgical support system may include both the modified procedure plan and a copy of the original procedure plan.

The invention claimed is:

1. A device comprising:
a processor configured to:
    receive first data indicative of a surgical patient, a target procedure, and a proposed procedure plan;
    generate a patient specific mapping from the first data via a first neural network trained independent of the target procedure, wherein the patient specific mapping indicates geometry data extracted by the first neural network;
    process, via a second neural network, the first data and the patient specific mapping that indicates the geometry data, wherein the second neural network is trained with data associated with the target procedure;
    obtain, from the second neural network, a modified procedure plan that is different from the proposed procedure plan; and
    send the proposed procedure plan and the modified procedure plan to a surgical support system.

2. The device of claim 1, wherein the first neural network is further trained to isolate anatomical elements.

3. The device of claim 1, wherein the processor configured to process, via the second neural network, the first data and the patient specific mapping further comprises the processor being further configured to:
    determine, via the second neural network, a correlation between the surgical patient and the target procedure based on the first data; and
    generate the modified procedure plan from the correlation via the second neural network.

4. The device of claim 3, wherein the proposed procedure plan and the modified procedure plan are sent to the surgical support system to cause the proposed procedure plan and the modified procedure plan to be displayed to a user.

5. The device of claim 1, wherein the first data comprises imaging data, procedure data, and patient-specific health data.

6. The device of claim 1, wherein the patient specific mapping comprises a data element indicative of patient anatomy targeted by the target procedure.

7. The device of claim 1, wherein the modified procedure plan reduces a complication rate associated with the target procedure.

8. The device of claim 1, wherein the patient specific mapping further indicates a registration based on a plurality of anatomical landmarks.

9. The device of claim 1, wherein the modified procedure plan indicates a port location associated with the geometry data, and wherein the proposed procedure plan does not indicate the port location.

10. The device of claim 1, wherein the modified procedure plan indicates a surgical instrument associated with the geometry data, and wherein the proposed procedure plan does not indicate the surgical instrument.

11. The device of claim 1, wherein the modified procedure plan indicates a tumor margin associated with the geometry data, and wherein the proposed procedure plan does not indicate the tumor margin.

12. The device of claim 1, wherein the modified procedure plan indicates a mobilization approach associated with the geometry data, and wherein the proposed procedure plan does not indicate the mobilization approach.

13. The device of claim 1, wherein data used to the train the first neural network is different from that used to the train the second neural network.

14. The device of claim 1, wherein an output of the first neural network corresponds to a data element used in the training of the second neural network.

15. A method comprising:
    receiving first data indicative of a surgical patient, a target procedure, and a proposed procedure plan;
    generating a patient specific mapping from the first data via a first neural network trained independent of the target procedure, wherein the patient specific mapping indicates geometry data extracted by the first neural network;
    processing, via a second neural network, the first data and the patient specific mapping that indicates the geometry data, wherein the second neural network is trained with data associated with the target procedure;
    obtain, from the second neural network, a modified procedure plan that is different from the proposed procedure plan; and
    sending the proposed procedure plan and the modified procedure plan to a surgical support system.

16. The method of claim 15, wherein the first neural network and the second neural network are independently trained.

17. The method of claim 15, wherein the method further comprises:
    determining, via the second neural network, a correlation between the surgical patient and the target procedure based on the first data; and
    generating the modified procedure plan from the correlation via the second neural network.

18. The method of claim 15, wherein an output of the first neural network corresponds to a data element used in the training of the second neural network.

19. A method comprising:
    training a first neural network independent of a target procedure;

training a second neural network with data associated with the target procedure;

inputting first data indicative of a surgical patient, the target procedure, and a proposed procedure plan to the first neural network to generate a patient specific mapping, wherein the patient specific mapping indicates geometry data extracted by the first neural network;

inputting the first data and the patient specific mapping that indicates the geometry data to the second neural network;

obtaining, from the second neural network, a modified procedure plan that is different from the proposed procedure plan; and sending the proposed procedure plan and the modified procedure plan to a surgical support system.

20. The method of claim 19, wherein the method further comprises:

determining, via the second neural network, a correlation between the surgical patient and the target procedure based on the first data; and generating the modified procedure plan from the correlation via the second neural network.

\* \* \* \* \*